(12) United States Patent
Wei et al.

(10) Patent No.: US 12,198,817 B2
(45) Date of Patent: Jan. 14, 2025

(54) METHOD, AND DEVICE FOR LOCALIZING AND LATERALIZING BRAIN FUNCTIONAL REGION, APPARATUS, AND STORAGE MEDIUM

(71) Applicant: BEIJING GALAXY CIRCUMFERENCE TECHNOLOGIES CO., LTD., Beijing (CN)

(72) Inventors: Coach Kecheng Wei, Beijing (CN); Weiwei Wang, Beijing (CN); Yuan Meng, Beijing (CN); Yezhe Wang, Beijing (CN)

(73) Assignee: BEIJING GALAXY CIRCUMFERENCE TECHNOLOGIES CO., LTD., Beijing (CN)

( * ) Notice: Subject to any disclaimer, the term of this patent is extended or adjusted under 35 U.S.C. 154(b) by 0 days.

(21) Appl. No.: 18/567,372

(22) PCT Filed: Feb. 15, 2022

(86) PCT No.: PCT/CN2022/076374
§ 371 (c)(1),
(2) Date: Dec. 6, 2023

(87) PCT Pub. No.: WO2022/257495
PCT Pub. Date: Dec. 15, 2022

(65) Prior Publication Data
US 2024/0290497 A1    Aug. 29, 2024

(30) Foreign Application Priority Data
Jun. 11, 2021 (CN) .......................... 202110655826.1

(51) Int. Cl.
G16H 50/30    (2018.01)
G16H 50/20    (2018.01)

(52) U.S. Cl.
CPC ............. *G16H 50/30* (2018.01); *G16H 50/20* (2018.01)

(58) Field of Classification Search
CPC ..... A61B 5/055; A61B 5/4064; A61B 5/0042; A61B 8/0808; A61B 5/4088;
(Continued)

(56) References Cited

U.S. PATENT DOCUMENTS

2015/0272469 A1* 10/2015 Fox .................. A61B 5/055
                                                   600/410
2015/0272493 A1* 10/2015 Liu .................. A61B 5/055
                                                   600/410
2019/0159712 A1*  5/2019 Marks ................ A61B 5/1176

FOREIGN PATENT DOCUMENTS

AU    2020102977 A1    12/2020
AU    2020102977 A4    12/2020
(Continued)

OTHER PUBLICATIONS

International search report received in the corresponding international application PCT/CN2022/076374, mailed May 17, 2022.
(Continued)

*Primary Examiner* — Aaron W Carter
*Assistant Examiner* — Courtney Joan Nelson
(74) *Attorney, Agent, or Firm* — Kilpatrick Townsend & Stockton LLP

(57) ABSTRACT

A method and a device for localizing and lateralizing a brain functional region, an electronic apparatus, and a storage medium are provided herein, wherein the method for localizing and lateralizing the brain functional region comprises: acquiring brain structural magnetic resonance imaging data
(Continued)

and brain functional magnetic resonance imaging data of a subject (201) based on the brain structural magnetic resonance imaging data and the brain functional magnetic resonance imaging data, determining a brain functional map of the subject (202), wherein the brain functional map comprises brain functional region identifiers of at least two brain functional regions and a corresponding set of voxels; for each of to-be-clinically-intervened voxels in a set of the to-be-clinically-intervened voxels, determining, based on the to-be-clinically-intervened voxel and the brain functional map, the brain functional region identifier corresponding to the to-be-clinically-intervened voxel (203); and determining a brain functional lateralization of the brain functional region of a target surgical region. Accurate and non-invasive preoperative localizing and lateralization of brain functional regions for individual subjects is achieved.

20 Claims, 8 Drawing Sheets

(58) Field of Classification Search
CPC .............. A61B 5/7267; A61B 5/7264; A61B 2576/026; A61B 5/0013; A61B 8/06; A61B 5/7275; A61B 5/48; G06T 2207/30016; G06T 7/0012; G06T 2207/10088; G06T 2207/20081; G06T 2200/04; G06T 2210/41; G06T 2207/30004; G06T 2219/004; G16H 30/40; G16H 50/30; G16H 50/20; G16H 30/20; G06V 10/764; G06V 10/25; G06V 2201/031; G06V 10/26
See application file for complete search history.

(56) References Cited

FOREIGN PATENT DOCUMENTS

| CN | 103345749 A | 10/2013 |
|---|---|---|
| CN | 105117731 A | 12/2015 |
| CN | 108961259 A | 12/2018 |
| CN | 111081351 A | 4/2020 |
| CN | 113450893 A | 9/2021 |

OTHER PUBLICATIONS

First office action received in the corresponding Chinese application 202110655826.1, mailed Sep. 30, 2022.
Notification of Grant of Invention Patent received in the corresponding Chinese application 202110655826.1, mailed Jan. 10, 2023.
Liu, Yongjian et al., "Functional MRI study of the functional language area with brain tumor preoperatively related with the semantic and syntactic paradigm", published on Journal of China Clinic Medical Imaging No. 8, Aug. 20, 2016.
Xiong, Xiaoshuang et al., "Study of functional MRI of two language tasks in normal subjects", published on Medical Journal of National Defending Forces in Southwest China No. 6, Jun. 20, 2009.
Hu, Ying et al., "Review on brain functional parcellation based on resting-state functional magnetic resonance imaging data" published on Journal of Image and Graphics No. 10, Oct. 16, 2017.
Wang, Kangcheng et al., "Segmentation and Application of Functional Brain Networks from Groups to Individuals", published on Chinese Science Bulletin No. 27, Sep. 30, 2016.
Shen, Yang et al., "Correlation study about lateralization of movement dysfunction and functional connectivity of movement cortical subregions in Parkinson's disease" published on Chinese Journal of Clinical Neurosciences No. 2, Mar. 20, 2020.
State Intellectual Property Office of the People's Republic of China, International Search Report Issued in Application No. PCT/CN2022/076374, May 17, 2022, 5 pages.
State Intellectual Property Office of the People's Republic of China, written opinion Issued in Application No. PCT/CN2022/076374, May 17, 2022, 11 pages.
Liu, Yong-jian et al., "Functional MRI study of the functional language area with brain tumor preoperatively related with the semantic and syntactic paradigm", Chin Clin Med Imaging, 2016, vol. 27, No. 8, total 6 pages.
Xiong, Xiao-shuang et al., "Study of functional MRI of two language tasks in normal subjects", Medical Journal of National Defending Forces in Southwest China , vol. 19, No. 6, total 3 pages.
Hu, Ying et al., "Review on brain functional parcellation based on resting-state functional magnetic resonance imaging data", Journal of Image and Graphics, vol. 22, No. 10, Oct. 2017, total 10 pages.
State Intellectual Property Office of the People's Republic of China, First Office Action Issued in Application No. 202110655826.1, Sep. 30, 2022, 10 pages.
State Intellectual Property Office of the People's Republic of China, Notification to Grant Patent Issued in Application No. 202110655826.1, Jan. 10, 2023, 3 pages.
Sheng, Yang et al., "The Motor Dysfunction Lateralization Influenced Functional Connectivity in Subregion of Motor Cortex in Parkinson's Disease", Chin J Clin Neurosci 2020, vol. 28, No. 2, total 9 pages.

* cited by examiner

200

201 — acquiring brain structural magnetic resonance imaging data and brain functional magnetic resonance imaging data of a subject 202 — determining a brain functional map of the subject based on the brain structural magnetic resonance imaging data and the brain functional magnetic resonance imaging data 203 — for each of to-be-clinically-intervened voxels in a set of to-be-clinically-intervened voxels, determining the corresponding brain functional region identifiers for the surgical voxel based on the surgical voxel and the brain functional map 204 — dividing the set of to-be-clinically-intervened voxels in accordance with the corresponding brain functional region identifiers for each to-be-clinically-intervened voxel to obtain at least one subset of brain functional region voxels of to-be-clinically-intervened voxels, with to-be-clinically-intervened voxels in each subset of brain functional region voxels of the to-be-clinically-intervened voxels corresponding to a same brain functional region identifier 205 — for each subset of brain functional region voxels of to-be-clinically-intervened voxels, determining, based on the brain functional map, a brain functional lateralization corresponding to the subset of brain functional region voxels of to-be-clinically-intervened voxels 206 — for each subset of brain functional region voxels of to-be-clinically-intervened voxels, determining a surgical risk value corresponding to the subset of brain functional region voxels of to-be-clinically-intervened voxels, based on the brain functional lateralization corresponding to the subset of brain functional region voxels of to-be-clinically-intervened voxels 207 — for each subset of brain functional region voxels of to-be-clinically-intervened voxels, determining a pixel value corresponding to the subset of brain functional region voxels of to-be-clinically-intervened voxels, based on the surgical risk value corresponding to the subset of brain functional region voxels of to-be-clinically-intervened voxels, and presenting the subset of brain functional region voxels of to-be-clinically-intervened voxels in accordance with the determined pixel value

FIG. 2

METHOD, AND DEVICE FOR LOCALIZING AND LATERALIZING BRAIN FUNCTIONAL REGION, APPARATUS, AND STORAGE MEDIUM

CROSS REFERENCE TO RELATED APPLICATIONS

This application is a national phase entry under 35 U.S.C. § 371 of International Application No. PCT/CN2022/076374, filed on Feb. 15, 2022, which claims priority to Chinese Patent Application No. 202110655826.1, filed on Jun. 11, 2021, the entire contents of all of which are incorporated herein by reference.

TECHNICAL FIELD

The present application relates to the field of computer technology and, in particular, to a method and a device for localizing and lateralizing a brain functional region, an apparatus and a storage medium.

BRIEF DESCRIPTION OF THE RELATED ART

Brain lateralization is an important organizing principle of the human brain and a potential marker of brain development. By studying the law of brain lateralization, it helps to understand the cognitive processing pattern of the human brain. In particular, precise localizing and lateralization of patients' brain functional activities is a key to improve clinical diagnosis and treatment. Currently, there is no risk-free, accurate, and reliable technical means for preoperative localizing and lateralization of brain functional regions in the surgical region. Therefore, there is a need for a safe and accurate localizing and lateralization technique to assist surgeons in planning brain surgery.

SUMMARY OF THE DISCLOSURE

The present application provides a method and a device for localizing and lateralizing a brain functional region, an electronic apparatus and a storage medium, so as to localize and lateralize the brain functional regions in a target surgical region.

In a first aspect, the present application provides a method of localizing and lateralization a brain functional region, the method comprising: acquiring brain structural magnetic resonance imaging data and brain functional magnetic resonance imaging data of a subject; determining a brain functional map of the subject based on the brain structural magnetic resonance imaging data and the brain functional magnetic resonance imaging data, wherein the brain functional map comprises brain functional region identifiers of at least two brain functional regions and a corresponding set of voxels; for each to-be-clinically-intervened voxel in a set of to-be-clinically-intervened voxels, determining the corresponding brain functional region identifier for the to-be-clinically-intervened voxel based on the to-be-clinically-intervened voxel and the brain functional map, wherein the brain functional region identifiers comprises the brain functional region identifier in the brain functional map; dividing the set of to-be-clinically-intervened voxels in accordance with the brain functional region identifier corresponding to each to-be-clinically-intervened voxel to obtain at least one subset of to-be-clinically-intervened brain functional region voxels, with to-be-clinically-intervened voxels in each subset of the to-be-clinically-intervened brain functional region voxels corresponding to a same brain functional region identifier; for each subset of to-be-clinically-intervened brain functional region voxels, determining, based on the brain functional map, a brain functional lateralization corresponding to the subset of to-be-clinically-intervened brain functional region voxels.

In some optional embodiments, the method further comprises:
for each subset of to-be-clinically-intervened brain functional region voxels, determining a surgical risk value corresponding to the subset of to-be-clinically-intervened brain functional region voxels, based on the brain functional lateralization corresponding to the subset of to-be-clinically-intervened brain functional region voxels.

In some optional embodiments, the method further comprises:
for each subset of to-be-clinically-intervened brain functional region voxels, determining a pixel value corresponding to the subset of to-be-clinically-intervened brain functional region voxels, based on the surgical risk value corresponding to the subset of to-be-clinically-intervened brain functional region voxels, and presenting the subset of voxels of to-be-clinically-intervened brain functional regions in accordance with the determined pixel value.

In some optional embodiments, determining a brain functional map of the subject based on the brain structural magnetic resonance imaging data and the brain functional magnetic resonance imaging data, comprising.
determining, based on the brain structural magnetic resonance imaging data, whether the brain structure of the subject has lesioned or not;
if the brain structure of the subject has no lesion, determining a brain functional map of the subject based on the brain functional magnetic resonance imaging data.

In some optional embodiments, determining the brain functional map of the subject based on the brain structure magnetic resonance imaging data and the brain function magnetic resonance imaging data, further comprising:
Determining a lesioned brain region and a non-lesioned brain region of the subject if the subject's brain has lesioned, wherein the lesioned brain region comprises M voxels, M being a positive integer greater than or equal to 2;
determining a brain functional map of the non-lesioned brain region based on the brain functional magnetic resonance imaging data, the brain functional map of the non-lesioned brain region comprising N brain functional regions, N being a positive integer greater than or equal to 2;
determining the correlation between each voxel in M voxels corresponding to the lesioned brain region and each brain functional region in the N brain functional regions;
for each voxel in the M voxel, determining, based on the correlation between the voxel and each of the N brain functional regions, the brain functional region corresponding to the voxel in accordance with a predetermined functional region classification rule, in order to obtain the brain functional map of the subject.

In some optional embodiments, determining, based on the correlation between the voxel and each of the N brain functional regions, the brain functional region corresponding to the voxel in accordance with a predetermined functional region classification rule comprises.

determining the brain functional region among the N brain functional regions having the highest correlation with the voxel as the brain functional region corresponding to the voxel.

In some optional embodiments, determining, based on the correlation between the voxel and each of the N brain functional regions, the brain functional region corresponding to the voxel in accordance with a predetermined functional region classification rule comprises.

in response to determining that the correlation between the voxel and each brain functional region of the N brain functional regions is less than a preset correlation threshold, determining the brain functional region corresponding to the voxel as an invalid brain functional region.

In some optional embodiments, determining, based on the correlation between the voxel and each of the N brain functional regions, the brain functional region corresponding to the voxel in accordance with a predetermined functional region classification rule comprises:

determining the brain functional region with the highest correlation with the voxel among the N brain functional regions as the brain functional region corresponding to the voxel, and obtaining a first iterative brain functional map of a lesioned brain region;

performing the following iterative operation: combining the first iterative brain functional map of the lesioned brain region with the brain functional map of the non-lesioned brain region to obtain an iterative brain functional map, the iterative brain functional map comprising N iterative brain functional regions; determining a correlation between the voxel and each iterative brain functional region among the N iterative brain functional regions; among the N brain functional regions, identifying the brain functional region with the highest correlation to the voxel as the brain functional region corresponding to the voxel, and obtaining the second iterative brain functional map of the lesioned brain region; determining whether the degree of match between the second iterative brain functional map of the lesioned brain region and the first iterative brain functional map of the lesioned brain region is greater than a preset threshold value of the degree of match; if yes, determining the second iterative brain functional map of the lesioned brain region as the brain functional map of the lesioned brain region, terminating the iterative operation, the brain functional map of lesioned brain region is used to characterize the brain functional region corresponding to the voxel; if not, updating the first iterative brain functional map of the lesioned brain region to be the second iterative brain functional map of the lesioned brain region and then continuing the iterative operation.

In some optional embodiments, determining, for each the subset of the to-be-clinically-intervened brain functional region voxels, a brain functional lateralization corresponding to the subset of the to-be-clinically-intervened brain functional region voxels based on the brain functional map, comprising:

determining, based on a hemispheric autonomy index of the brain functional region corresponding to the subset of the to-be-clinically-intervened brain functional region voxels, the brain functional lateralization corresponding to the subset of the to-be-clinically-intervened brain functional region voxels;

or, determining the brain functional lateralization corresponding to the subset of the to-be-clinically-intervened brain functional region voxels based on areas of left and right lateral functional region surfaces of the brain functional region corresponding to the subset of the to-be-clinically-intervened brain functional region voxels.

In some optional embodiments, the surgical risk value comprises a left side risk value and a right side risk value; and determining a surgical risk value corresponding to the subset of the to-be-clinically-intervened brain functional region voxels based on the brain function lateralization corresponding to the subset of the to-be-clinically-intervened brain functional region voxels, comprising:

determining the left side risk value and the right side risk value corresponding to the subset of the to-be-clinically-intervened brain functional region voxels based on the brain function lateralization corresponding to the subset of the to-be-clinically-intervened brain functional region voxels.

In some optional embodiments, the brain functional map further comprises a functional connectivity confidence level between two different voxels; and the step of determining the pixel value corresponding to the subset of the to-be-clinically-intervened brain functional region voxels based on the surgical risk value corresponding to the subset of the to-be-clinically-intervened brain functional region voxels, further comprising:

determining the functional connectivity confidence level of each voxel of the subset of the to-be-clinically-intervened brain functional region voxels as a weight of the risk value to obtain a risk weight matrix;

determining a left side risk weight matrix and a right side risk weight matrix based on the risk weight matrix;

determining a left side pixel value corresponding to the subset of the to-be-clinically-intervened brain functional region voxels based on the left side risk weight matrix and the left side risk value;

determining a right side pixel value corresponding to the subset of the to-be-clinically-intervened brain functional region voxels based on the right side risk weight matrix and the right side risk value;

determining a pixel value corresponding to the subset of the to-be-clinically-intervened brain functional region voxels based on the left side pixel value and the right side pixel value.

In the second aspect, the present application provides a device for localizing and lateralizing a brain functional region, comprising:

a data acquiring unit, configured to acquire brain structural magnetic resonance imaging data and brain functional magnetic resonance imaging data of a subject;

a processing unit, configured to determine a brain functional map of the subject based on the brain structural magnetic resonance imaging data and the brain functional magnetic resonance imaging data, wherein the brain functional map comprises brain functional region identifiers of at least two brain functional regions and a corresponding set of voxels;

a localizing unit, configured to determine, for each to-be-clinically-intervened voxel in a set of to-be-clinically-intervened voxels, a brain functional region identifier corresponding to the to-be-clinically-intervened voxel based on the to-be-clinically-intervened voxel and the brain functional map, wherein the brain functional region identifier comprises the brain functional region identifier in the brain functional map;

a lateralizing unit, configured to divide the set of to-be-clinically-intervened voxels in accordance with the brain functional region identifier corresponding to the respective to-be-clinically-intervened voxel, obtain at least one subset of the to-be-clinically-intervened brain functional region voxels, to-be-clinically-intervened voxels in each subset of the to-be-clinically-intervened brain functional region voxels correspond to the same brain functional region identifier, and for each subset of the to-be-clinically-intervened brain functional region voxels, based on the brain functional map, determine brain functional lateralization corresponding to the subset of the to-be-clinically-intervened brain functional region voxels.

In some optional embodiments, the device further comprises:
a risk value determining unit, configured to determine, for each subset of to-be-clinically-intervened brain functional region voxels, a surgical risk value corresponding to the subset of to-be-clinically-intervened brain functional region voxels based on the brain function lateralization corresponding to the subset of the to-be-clinically-intervened brain functional region voxels.

In some optional embodiments, the device further comprises:
a presenting unit, configured to determine, for each subset of the to-be-clinically-intervened brain functional region voxels, a pixel value corresponding to the subset of the to-be-clinically-intervened brain functional region voxels, based on the surgical risk value corresponding to the subset of the to-be-clinically-intervened brain functional region voxels, and to present the subset of the to-be-clinically-intervened brain functional region voxels accordance with the determined pixel value.

In some optional embodiments, the processing unit, is further configured to:
determine, based on the brain structural magnetic resonance imaging data, whether the brain structure of the subject has lesioned or not;
if the brain structure of the subject has no lesion, determine a brain functional map of the subject based on the brain functional magnetic resonance imaging data.

In some optional embodiments, the processing unit, is further configured to:
determine a lesioned brain region and a non-lesioned brain region of the subject if the subject has a lesioned brain structure, wherein the lesioned brain region comprises M voxels, M being a positive integer greater than or equal to 2; determine a brain functional map of the non-lesioned brain region based on the brain functional magnetic resonance imaging data, the brain functional map of the non-lesioned brain region comprising N brain functional regions, N being a positive integer greater than or equal to 2;
determine a correlation between each voxel in M voxels corresponding to the lesioned brain region and each brain functional region in the N brain functional regions;
for each voxel in the M voxel, determine, based on the correlation between the voxel and each of the N brain functional regions, the brain functional region corresponding to the voxel in accordance with a predetermined functional region classification rule, in order to obtain the brain functional map of the subject.

In some optional embodiments, the processing unit, is further configured to:
determine the brain functional region among the N brain functional regions having the highest correlation with the voxel as a brain functional region corresponding to the voxel.

In some optional embodiments, the processing unit, is further configured to:
in response to determining that the correlation between the voxel and each brain functional region of the N brain functional regions is less than a preset correlation threshold, determining the brain functional region corresponding to the voxel as an invalid brain functional region.

In some optional embodiments, the processing unit, is further configured to:
determine the brain functional region with the highest correlation with the voxel among the N brain functional regions as the brain functional region corresponding to the voxel, and obtaining a first iterative brain functional map of a lesioned brain region;
perform the following iterative operation: combining the first iterative brain functional map of the lesioned brain region with the brain functional map of the non-lesioned brain region to obtain an iterative brain functional map, the iterative brain functional map comprising N iterative brain functional regions; determining a correlation between the voxel and each iterative brain functional region among the N iterative brain functional regions; among the N brain functional regions, identifying the brain functional region with the highest correlation to the voxel as the brain functional region corresponding to the voxel, and obtaining the second iterative brain functional map of the lesioned brain region; determining whether the degree of match between the second iterative brain functional map of the lesioned brain region and the first iterative brain functional map of the lesioned brain region is greater than a preset threshold value of the degree of match; if yes, determining the second iterative brain functional map of the lesioned brain region as the brain functional map of the lesioned brain region, terminating the iterative operation, the brain functional map of the lesioned brain region is used to characterize the brain functional region corresponding to the voxel; if not, updating the first iterative brain functional map of the lesioned brain region to be the second iterative brain functional map of the lesioned brain region and then continuing the iterative operation.

In some optional embodiments, the lateralizing unit, is further configured to:
determine, based on a hemispheric autonomy index of the brain functional region corresponding to the subset of the to-be-clinically-intervened brain functional region voxels, the brain functional lateralization corresponding to the subset of the to-be-clinically-intervened brain functional region voxels:
or, determine the brain functional lateralization corresponding to the subset of the to-be-clinically-intervened brain functional region voxels based on areas of left and right lateral functional region surfaces of the brain functional region corresponding to the subset of the to-be-clinically-intervened brain functional region voxels.

In some optional embodiments, the risk value determining unit is further configured to:
based on the brain functional lateralization corresponding to the subset of the to-be-clinically-intervened voxels, determine the left risk value and the right risk value corresponding to the subset of the to-be-clinically-intervened voxels.

In some optional embodiments, the brain functional map further comprises a functional connectivity confidence level between two different voxels, and the presenting unit is further configured to:

determine the functional connectivity confidence level of each voxel of the subset of the to-be-clinically-intervened brain functional region voxels as a weight of the risk value to obtain a risk weight matrix;

determine a left side risk weight matrix and a right side risk weight matrix based on the risk weight matrix;

determine a left side pixel value corresponding to the subset of the to-be-clinically-intervened brain functional region voxels based on the left side risk weight matrix and the left side risk value;

determine a right side pixel value corresponding to the subset of the to-be-clinically-intervened brain functional region voxels based on the right side risk weight matrix and the right side risk value;

determine a pixel value corresponding to the subset of the to-be-clinically-intervened brain functional region voxels based on the left side pixel value and the right side pixel value.

In a third aspect, the present disclosure provides an electronic apparatus, including: one or more processors;

a storage device having one or more programs stored thereon, wherein the one or more programs, when executed by the one or more processors, causes the one or more processors to execute the method according to any one of embodiments of the first aspect.

In a fourth aspect, the present disclosure provides a computer readable storage medium having a computer program stored thereon, wherein the computer program, when executed by one or more processors, execute the method according to any one of embodiments of the first aspect.

In order to achieve localizing and lateralizing the brain functional region, current commonly used technological means include:

1. Intraoperative arousal electrical stimulation, waking the patient from anesthesia state before removing the lesion, using neurophysiological technology to accurately localize the functional regions of the brain and inquire about the relationship between the lesion and the functional regions, is currently the main method of localizing the functional region before surgery. Disadvantages are: to need craniotomy, having high surgical risk, prone to complications such as respiratory obstruction, respiratory depression, seizures, increased intracranial pressure, etc. during or after surgery, and may increase the chances of recurrence of the lesion.
2. Wada Test (through the method of cerebral angiography, respectively, puncturing the bilateral common carotid artery or through the femoral artery intubation, injection of isobarbital and other related anesthetic drugs to achieve anesthesia one side of the brain, so that the anesthetized side of the brain is in the function of the transient state of inhibition, through the patient's language and memory and other tests, judging and thus observing the speech, memory and other behavioral performance of the contralateral cerebral hemisphere), is currently the main method to determine the side of brain function in clinical practice. Shortcomings are: Wada test is invasive at a certain degree, patients are prone to complications, such as epileptic seizures, stroke and transient ischemic lesions, etc., in addition to allergies and infections, it is complicated operation, expensive, low application rate; the test can only be used to find the functionally dominant side of the brain function lateralization, and can not be used to localize the functional regions more accurately.
3. Based on the task-based functional magnetic resonance lateralizing and localizing method, by performing specific tasks, brain functional activation regions are located, the lateralization index is calculated and specific functional regions are identified; for example, to observe the localizing and lateralizing of language functional regions in patients with language functional region-related brain tumors, the subjects will do some semantic and grammatical sentence correctness judgment tasks, and the regions of bilateral middle frontal gyrus, bilateral supramedian frontal gyrus, bilateral supramedian temporal gyrus, and the left inferotemporal gyrus will be activated, and these activated regions are identified as language function regions, and then the language function lateralization index is calculated. Shortcomings are: the results are very dependent on the design of the task and the patient's cooperation with the task during the scanning process, but in many cases, patients (especially children, cognitively impaired patients, and patients with severe functional impairments) are not able to cooperate effectively with the task execution.
4. Based on the resting state functional magnetic resonance lateralizing and localizing method, the resting state refers to the existence of a large number of spontaneous neuronal activities in the waking state of the human brain, the performance of which is dependent on the signal of the level of blood oxygen, and the low-frequency oscillations in the resting state show a high degree of synchronicity between different brain regions within the brain functional network, and the lateralizing and localizing based on the data of the magnetic resonance in the resting state, for example, based on the strength of the functional connectivity of the left and right brains. Shortcomings are: most of the current lateralizing and localizing methods of the functional region based on the resting-state functional magnetic resonance method are less sensitive and less accurate.

The present application provides a method and a device for localizing and lateralizing a brain functional region, an apparatus and a storage media. Brain structural magnetic resonance imaging data and brain functional magnetic resonance imaging data of the subject are firstly acquired, wherein the brain functional magnetic resonance imaging data includes a blood oxygen level-dependent BOLD signal sequence corresponding to each voxel in a predetermined number of voxels; and then, based on the brain structural magnetic resonance imaging data and the brain functional magnetic resonance imaging data, the brain functional map of the subject is determined, wherein the brain functional map comprises a plurality of brain functional regions; for each of the to-be-clinically-intervened voxels in the set of to-be-clinically-intervened voxels, the brain functional region identifiers corresponding to such to-be-clinically-intervened voxel are determined based on the to-be-clinically-intervened voxel and the brain functional map; the set of to-be-clinically-intervened voxels is divided in accordance with the identifiers of the brain functional regions corresponding to the to-be-clinically-intervened voxels, obtaining at least one subset of the to-be-clinically-intervened brain functional region voxels, to-be-clinically-intervened voxels in each subset of to-be-clinically-intervened brain functional region voxels correspond to the same brain functional region identifier; and for each subset of to-be-clinically-intervened brain functional region voxels, the brain functional lateralization corresponding to the subset of to-be-clinically-intervened brain functional region voxels is determined on the basis of the brain functional map. In other words, through the subject-based personalized brain functional region profiling technique, the brain functional region and brain functional lateralization can be localized by the brain functional magnetic resonance imaging data, which can non-invasively detect the human brain function, accurately localize and lateralize the brain functional regions, and provide a strong support for the doctor to carry out the planning of the brain surgery. It can effectively solve the problems of inaccurate localizing and lateralizing of functional regions due to the lack of consideration of individual structural or functional differences in traditional methods, and the complications that may easily occur after surgery.

BRIEF DESCRIPTION OF THE DRAWINGS

Various embodiments discussed herein will be generally shown in drawings by way of example, without limitation.

FIG. 2 is a flow schematic diagram of an embodiment of a method for localizing and lateralizing brain functional regions according to the present application;

DETAILED DESCRIPTION OF THE PREFERRED EMBODIMENT

In order that the characteristics and technical contents of the embodiments of the present disclosure can be understood in detail, a more particular description on how to implement the embodiments of the disclosure will be given by reference to the accompanying drawings. These drawings are only intended to illustrate, but are not intended to limit the embodiments of the disclosure.

It should be noted that the terms "first\second\third" related to the embodiments of the present disclosure are only used to distinguish similar objects, but do not mean a specific ordering for the objects And it should be understood that "first\ second \ third" may be interchanged in the specific order or sequence when allowed. It should be noted that the objects defined by "first\second\third" may be interchanged under appropriate circumstances such that embodiments of the disclosure described herein may be implemented in orders other than those illustrated or described herein.

Figure 1:
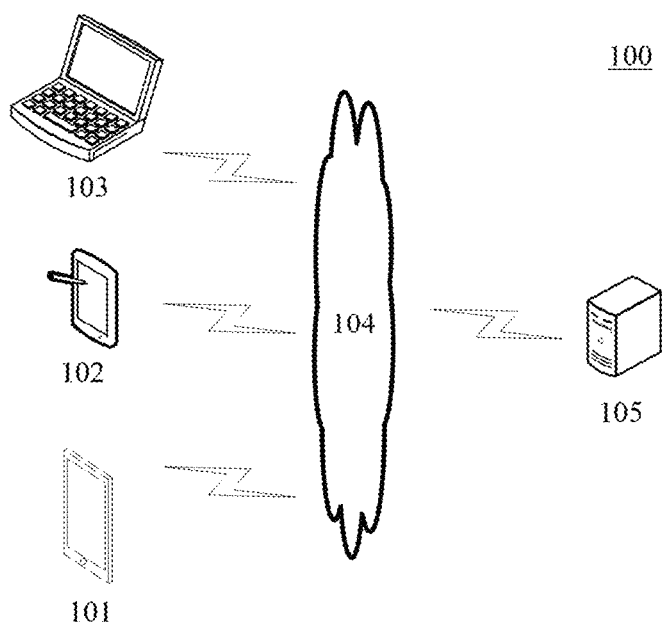
FIG. 1 is an exemplary system architecture diagram in which an embodiment of the present disclosure may be applied.

FIG. 1 illustrates an exemplary system architecture 100 in which embodiments of a method for localizing and lateralizing a brain functional region or a device for localizing and lateralizing a brain functional region of the present disclosure can be applied.

As shown in FIG. 1, the system architecture 100 can include terminal devices 101, 102, 103, a network 104, and a server 105. The network 104 is a medium used to provide communication links between the server 105 and each of the terminal devices 101, 102, 103. The network 104 may include various connection types, such as wired communication links, wireless communication links, or fiber optic cables, and so on.

Users may use terminal devices 101, 102, 103 to interact with the server 105 over the network 104 to receive or transmit messages or the like. Various communication client applications, such as a magnetic resonance imaging control application, a functional magnetic resonance imaging control application, a web browser application, a shopping application, a search application, an instant messaging tool, a mailbox client, social platform software, and the like, may be installed on the terminal devices 101, 102, and 103.

The terminal devices 101, 102, 103 can be implemented by hardware or software. When the terminal devices 101, 102, 103 are implemented by hardware, they may be various electronic devices with display screens, including but not limited to smart phones, tablet computers, laptop portable computers, desktop computers, and the like. When the terminal devices 101, 102, 103 are implemented by software, they can be installed in the above-listed electronic devices. It may be implemented as a plurality of software or software modules (e.g. processing for providing the brain structural magnetic resonance imaging data or the brain functional magnetic resonance imaging data) or as a single software or software module. It is not particularly limited herein.

The server 105 can be a server that provides various services, such as a background data processing server that processes magnetic resonance imaging data transmitted by the terminal devices 101, 102, 103. The background data processing server can determine the brain functional map of the subject based on the brain structural magnetic resonance imaging data or the brain functional magnetic resonance imaging data, and send them back to the terminal devices.

It should be noted that the server 105 can be implemented by hardware or software. When the server 105 is implemented by hardware, it may be implemented as a distributed server cluster composed of a plurality of servers, or may be implemented as a single server. When the server 105 is implemented by software, it may be implemented as multiple software or a software module (e.g., to provide distributed services), or as single software or a software module. It is not particularly limited herein It should be noted that the method for localizing and lateralizing brain functional regions provided by the present disclosure is generally performed by the server 105, and accordingly, the device for localizing and lateralizing brain functional regions is generally disposed in the server 105.

It should be noted that, in some cases, the method for localizing and lateralizing brain functional regions provided by the present disclosure may be executed by the server 105, by the terminal devices 101, 102, and 103, or both the server 105 and the terminal devices 101, 102, and 103. Accordingly, the device for localizing and lateralizing brain functional regions may be disposed in the server 105, or may be disposed in the terminal devices 101, 102, and 103, or may be disposed partially in the server 105 or partially in the terminal devices 101, 102, and 103. And accordingly the system architecture 100 can include only the server 105, or only the terminal devices 101, 102, 103, or can include the terminal devices 101, 102, 103, the network 104 and the server 105. It is not particularly limited in the present disclosure.

It should be understood that the numbers of the terminal devices, the network, and the server in FIG. 1 is merely illustrative. There may be any number of terminal devices, networks, and servers, as desired for an implementation.

Next, with reference to FIG. 2, a flow 200 of an embodiment of a method of localizing and lateralizing brain functional regions according to the present application is shown. The method of localizing and lateralizing brain functional regions includes the following steps:

Step 201, the brain structural magnetic resonance imaging data and the brain functional magnetic resonance imaging data of a subject is acquired.

In this embodiment, an executing subject (e.g., the server shown in FIG. 1) of method of localizing and lateralizing brain functional regions may first locally or remotely acquire brain structural magnetic resonance imaging data and brain functional magnetic resonance imaging data of the subject from other electronic apparatus (e.g., the terminal device shown in FIG. 1) connected to the network of the executing subject.

In an embodiment of the present application, the brain structural magnetic resonance imaging data comprises data obtained by performing structural magnetic resonance imaging on a brain of the subject, and the brain functional magnetic resonance imaging data comprises data obtained by performing functional magnetic resonance imaging on the brain of the subject, wherein the brain functional magnetic resonance imaging data comprises a sequence of Blood Oxygen Level Dependency (BOLD) signals corresponding to each of the predetermined number of voxels.

The data obtained from functional magnetic resonance imaging contains information of time series, which is equivalent to a four-dimensional image. For example, if a functional magnetic resonance imaging image is acquired with a 3-dimensional image matrix (Length×Width×Height, L×M×N), and one frame is acquired every 2 seconds, then 150 frames of data can be acquired in 6 minutes, forming a functional magnetic resonance imaging data signal of L×M×N×150.

The data obtained from magnetic resonance imaging is a high-resolution three-dimensional gray-scale image of anatomical structures, such as T1w (T1-weighted imaging-salient tissue T1 relaxation (longitudinal relaxation) difference) and its associated images, T2w (T2-weighted imaging—salient tissue T2 relaxation (transverse relaxation) difference) and its associated images, Fluid Attenuated Inversion Recovery Sequence (FLAIR) and its associated images, and the like.

In embodiments of the present application, the functional magnetic resonance imaging may include: task-based functional magnetic resonance imaging, and/or, resting state functional magnetic resonance imaging.

It will be appreciated that the resting state functional magnetic resonance imaging is magnetic resonance imaging obtained by performing a magnetic resonance scan of the subject's brain while the subject is not performing any task during the scan. The task-based functional magnetic resonance imaging is magnetic resonance imaging obtained by performing a magnetic resonance scan of the subject's brain while the subject is performing a target task. In some embodiments of the present application, functional magnetic resonance imaging data of the brain of the subject can be obtained by resting-state functional magnetic resonance imaging, reducing the complexity of the examination and reducing the dependence on the state of the patient and the cooperation in performing the task, when it is not requiring the cooperation of the patient in performing the task.

After obtaining the brain structural magnetic resonance scanning data of the subject, various implementations can be used to determine the structural brain map of the subject based on the brain structural magnetic resonance scanning data of the subject, i.e., to obtain those specific regions of the brain of the subject are what structural components. For example, it can be implemented using existing software (such as FreeSurfer, a software package for the analysis and visualization of structural and functional neuroimaging data) for processing 3D brain scan data. As another example, it is also possible to train a deep learning model based on a large amount of brain structure image scan sample data and the annotation of the corresponding brain structural components in advance, and then input the subject's brain structure MRI scan data into the trained deep learning model and obtain the corresponding brain structure map.

In some optional embodiments, the above-described executing subject, after acquiring the brain structural magnetic resonance imaging data and the brain functional magnetic resonance imaging data of the subject, pre-processes the brain structural magnetic resonance imaging data and the brain functional magnetic resonance imaging data. In the present application, the processing method for the pre-processing is not specifically limited, and exemplarily, the pre-processing may include the following.

Preprocessing of the brain structural magnetic resonance imaging data may include, for example, skull removal, field intensity correction, individual anatomical structure segmentation, cerebral cortex reconstruction and the like.

Preprocessing of the brain functional magnetic resonance imaging data, for example, can include the following steps:
(1) slice timing, head motion correction, temporal signal filtering, noise component regression, spatial smoothing, etc.;
(2) registering image of the brain functional magnetic resonance imaging data with the structural image;
(3) projecting signals of the brain functional magnetic resonance imaging data onto the structural image.

Here, the structural image may include the brain structural magnetic resonance imaging data of the subject, a reconstructed structural image of the brain cortex based on the brain structural magnetic resonance imaging data of the subject, or a structural image of the brain averaged level over the relevant group.

Step 202, based on the brain structural magnetic resonance imaging data and the brain functional magnetic resonance imaging data, a brain functional map of the subject is determined.

Here, the brain functional map may include brain functional region identifiers of at least two brain functional regions and a corresponding set of voxels. The exact number of brain functional regions may be determined based on the actual desired division, exemplarily, in some practical applications, the brain functional map may include from 2 to 1000 brain functional regions.

Brain functional map (abbreviated as "brain map" or "functional map" or "brain functional network map") refers to the map formed by dividing the cerebral cortex into functional regions of the brain, and marking out the different regions of the brain that are responsible for different functions; the labeled regions are also known as the "functional regions" or "functional networks", i.e., the brain functional regions.

Figure 3:
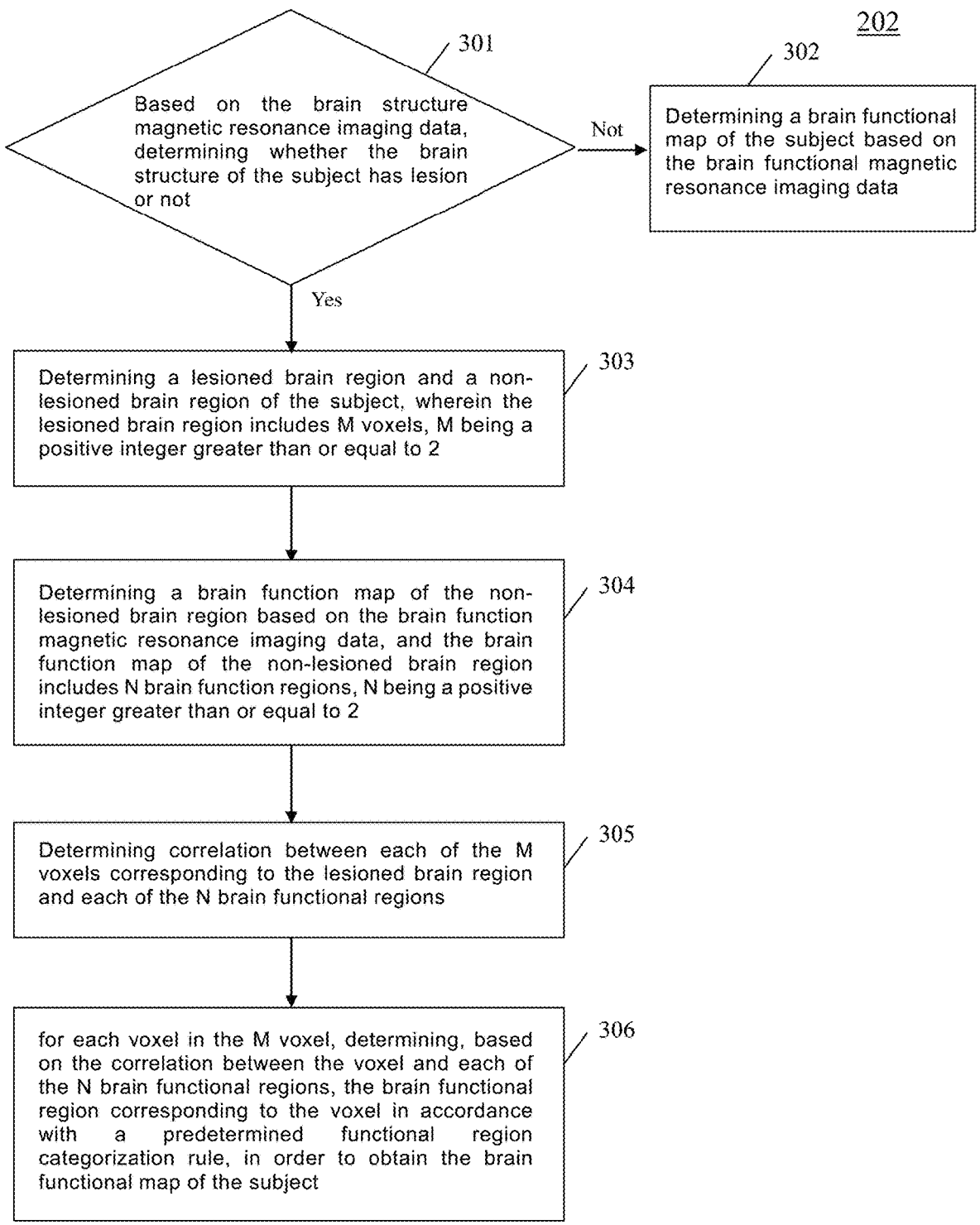
FIG. 3 is a schematic diagram of a disassembled flow of an embodiment of step 202 of the method for localizing and lateralizing brain functional regions shown in FIG. 2.

FIG. 3 is a schematic diagram of a disassembled flow of step 202 in the method for localizing and lateralizing brain functional regions shown in FIG. 2. In some optional embodiments, the above step 202 may specifically include the following steps.

Step 301, based on the brain structure magnetic resonance imaging data, a determination is made as to whether the brain structure of the subject has lesion. If not, step 302 is performed; if yes, step 303 is performed.

In the present application, lesion to the brain structure refers to a situation where the brain structure has a lesion such as a defect, an occupancy, etc., compared to the intact standard human brain anatomy, e.g., a defect in the brain structure caused by a previous clinical intervention or caused by a trauma, a vacancy of the brain structure caused by localized brain atrophy, or loss of the brain structure caused by a tumor occupancy.

Here, it may be determined whether the brain structure of the subject has lesion based on a comparison of the brain structure magnetic resonance imaging data with standard brain structure modeling data or, alternatively, it may be determined whether the brain structure of the subject in the brain structure magnetic resonance imaging data has lesion based on a medical diagnosis.

Step 302, a brain functional map of the subject is determined based on the brain functional magnetic resonance imaging data.

The cluster-level brain functional maps are first projected onto the subject's brain functional magnetic resonance imaging data, after which a recursive algorithm is used to progressively adjust the boundaries of these functional regions based on the subject's brain functional magnetic resonance imaging data until the results of the network profiling are stabilized or an iterative termination condition is met, e.g., the number of iterations reaches a preset value. The recursive process will utilize the patient's distribution of individual differences in brain connectivity, as well as the patient's own signal-to-noise ratio of brain images, to determine the magnitude of network boundary adjustment. Finally, we will fuse the functional networks obtained for each anatomical region according to the correlation of signals, thus obtaining a brain functional map of the subject, and ultimately 2 to 1000 functional regions can be identified in the whole brain according to the actual needs.

In the present application, the brain functional map may comprise a two-dimensional surface-based brain functional map or a three-dimensional volume-based brain functional map.

Step 303, determining a lesioned brain region and a non-lesioned brain region of the subject, wherein the lesioned brain region includes M voxels, M being a positive integer greater than or equal to 2.

The lesioned brain region of the subject may be determined based on the brain structure magnetic resonance imaging data, e.g., by comparing the standard brain structure imaging data with the subject's brain structure magnetic resonance imaging data, a region of the subject's brain structure magnetic resonance imaging data that has a structural brain defect in relation to the standard brain structure imaging data is determined to be the lesioned brain region of the subject.

lesioned brain regions and non-lesioned brain regions of a subject may be determined by making a lesioned brain region mask and a non-lesioned brain region mask.

A mask is a binary image consisting of 0 and 1, and in this application, the mask may be a 2D or 3D mask corresponding to a brain functional map. When a mask is applied to a certain function, 1-value regions are processed and masked 0-value regions are not included in the calculation. Image masks are defined by specified data values, data ranges, finite or infinite values, regions of interest, and annotation files, and masks can also be created by applying any combination of the above options as input.

Here, the manner of determining the lesioned brain region mask may include one of the following:

(1) obtaining a mask of the lesioned brain region manually drawn by a physician based on experience.
(2) determining which structures are involved based on the region of lesion by using an existing structural partition template, such as an automated anatomical labeling map template, a Brodmann map, or a Desikan-Killiany map, and combining these structures as a lesioned brain region mask.
(3) by using existing brain functional partition templates, such as the Yeo 17 functional network template, determining which functional regions are involved based on the region of lesion, and combining these functional regions as a lesioned brain region mask.
(4) determining the lesioned brain region mask by machine learning, deep learning, etc. The non-lesioned brain region is the region other than the lesioned brain region, which can be obtained by subtracting the lesioned brain region from the whole brain region.

Step 304, a brain function map of the non-lesioned brain region is determined based on the brain function magnetic resonance imaging data, and the brain function map of the non-lesioned brain region includes N brain function regions, N being a positive integer greater than or equal to 2.

Here, the brain functional map of the non-lesioned brain region may be determined in the same manner as the general brain functional map, such as the manner of determining the brain functional map in step 302, which will not be repeated herein.

Step 306, the correlation between each of the M voxels corresponding to the lesioned brain region and each of the N brain functional regions is determined.

In the present application, for the determination of the correlation, it may be obtained by calculating the BOLD signal sequence corresponding to the voxel. Exemplarily, the BOLD signal sequence corresponding to each voxel comprises T BOLD values, T being the number of sampling in the time dimension corresponding to the scanning time, wherein the correlation between the two voxels may be calculated based on the T BOLD values corresponding to the voxels by a Pearson correlation coefficient, and the correlation between the voxels and the brain functional region may be calculated based on an average of the BOLD signal sequence corresponding to the voxels and the BOLD signal sequence of each voxel in the brain functional region by Pearson's correlation coefficient.

In the present disclosure, the correlation coefficient is a Pearson's correlation coefficient, which is a coefficient used to measure a linear degree between variables. The calculation formula thereof is as follows:

$$\rho_{X,Y} = \frac{\text{cov}(X,Y)}{\sigma_X \sigma_Y} = \frac{E((X-\mu_X)(Y-\mu_Y))}{\sigma_X \sigma_Y} = \frac{E(XY) - E(X)E(Y)}{\sqrt{E(X^2) - E^2(X)} \sqrt{E(Y^2) - E^2(Y)}}$$

The formula is defined as: the Pearson's correlation coefficient $\rho_{(x,y)}$ of two consecutive variables $(X, Y)$ is equal to the covariance cov (X, Y) between them divided by the product of their respective standard deviations ($\sigma_X$, $\sigma_Y$). Coefficients are always values between −1.0 and 1.0. If variables approximately equal to 0, it will be called as having no correlation. In contrast, if variables approximately equal to 1 or −1, it will be called as having strong correlation.

Step 307, for each voxel in the M voxels, the brain functional regions corresponding to the voxels are determined according to correlation between the voxels and each brain functional region in the N brain functional regions in accordance with a predetermined functional region classification rule, in order to obtain a brain functional map of the subject.

For the above step 307, it is to be understood that since the brain functional map of the non-lesioned brain functional region has been determined at step 305, i.e., the brain functional region corresponding to each voxel in the non-lesioned brain functional region of the subject has been determined, after determining the brain functional region corresponding to each of the M voxels which correspond to the lesioned brain region, i.e., the brain functional region corresponding to each of the voxels in the whole-brain brain functional magnetic resonance imaging data of the subject is determined, which in turn results in the brain functional map of the subject.

As a result, brain functional region identifiers can be determined for each of the M voxels in the lesioned brain region.

In some optional embodiments, the above step 307 may specifically include:

identifying the brain functional region among the N brain functional regions that has the highest correlation with the voxel as the brain functional region corresponding to the voxel.

In this way, the brain functional regions of the M voxels in the lesioned brain region can be quickly determined, and each voxel corresponds to the brain functional region in the non-lesioned brain region that has the highest correlation with it, and the correlation between the various parts of the lesioned brain region and the corresponding brain functional regions in the non-lesioned brain region can be clearly labeled.

In some optional embodiments, the above step 307 may specifically include:

If each of the N brain functional regions has a correlation with the voxel, and the correlation is less than a predetermined threshold of the correlation, identifying the brain functional region corresponding to the voxel as an invalid brain functional region.

in the application, invalid brain functional regions may include regions that do not have significant functional correlation with non-lesioned brain regions of the subject. For example, in patients with brain tumors, some of the vertices or voxels of the tumor region have low functional connectivity to the whole brain, they can be classified as an invalid brain functional region, and the removal or destruction of this functional region will not cause functional lesion to the patient; to give another example such as in patients with necrotic brain tissue, the necrotic portion of the brain tissue is completely functionally lost after the cessation of cellular metabolism and there is no functional connectivity between vertices or voxels of the necrotic region of the brain and the whole brain, they can be categorized as the invalid brain functional regions, and the remaining voxels are redistributed according to the functional region with the strongest correlation coefficient with them. Here, the preset threshold of the correlation can be set according to actual needs, for example, 0.2.

Figure 4:
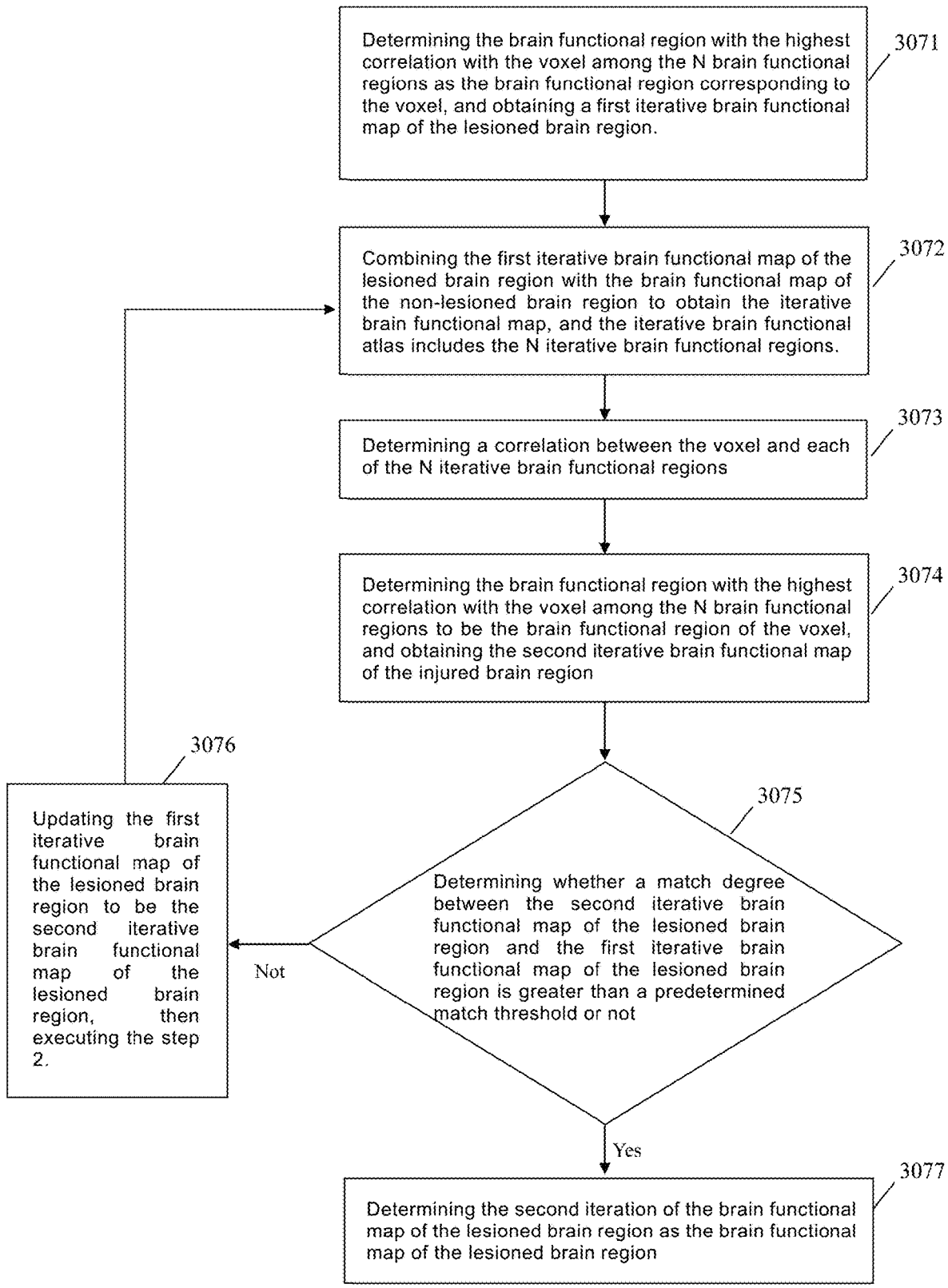
FIG. 4 is a schematic diagram of the disassembled flow of an embodiment of step 306 shown in the embodiment of FIG. 3.

FIG. 4 is a schematic diagram of the decomposed flow of step 307 in the embodiment shown in FIG. 3. In some optional embodiments, the above step 307 may specifically include:

Step 3071, the brain functional region with the highest correlation with the voxel among the N brain functional regions is determined as the brain functional region corresponding to the voxel, and a first iterative brain functional map of the lesioned brain region is obtained.

Step 3072, the first iterative brain functional map of the lesioned brain region is combined with the brain functional map of the non-lesioned brain region to obtain the iterative brain functional map, and the iterative brain functional map includes the N iterative brain functional regions.

Step 3073, correlation between the voxels and each of the N iterative brain functional regions is determined.

Step 3074, the brain functional region with the highest correlation with the voxel among the N brain functional regions are determined to be the brain functional region of the voxel, and the second iterative brain functional map of the lesioned brain region is obtained.

Step 3075, it is to determine whether a match degree between the second iterative brain functional map of the lesioned brain region and the first iterative brain functional map of the lesioned brain region is greater than a predetermined match threshold, and if not, it is to perform step 3076, and if yes, it is to perform step 3077.

In some optional embodiments, step 3075 further comprises: determining a number of executions of step 3075, and if the number of executions reaches a predetermined threshold number of cycles, executing step 3077.

Step 3076, step 3072 is executed after updating the first iterative brain functional map of the lesioned brain region in step 3072 to a second iterative brain functional map of the lesioned brain region.

Step 3077, the second iterative brain functional map of the lesioned brain region is determined as the brain functional map of the lesioned brain region.

Where the brain functional map of the lesioned brain region is used to characterize the brain functional region corresponding to the voxel.

The brain functional map for each voxel in the lesioned brain region is continuously corrected by means of iterative calculations to make the obtained brain functional map of the lesioned brain region more accurate.

In some optional embodiments, the above step 307 may comprise: determining a correlation of each voxel in the lesioned brain region with each functional region of the N functional regions of the non-lesioned brain region, determining the functional region of each voxel in the functional region of the lesioned brain region that has the highest correlation with the N functional regions, as a functional region of the voxel, obtaining a brain functional map of the lesioned brain region and combining it with the brain functional map of the non-lesioned brain region to create a new whole-brain functional map, followed by using a recursive algorithm, the recursive algorithm comprising calculating a correlation coefficient between each voxel in the lesioned brain region and each functional region of the new whole-brain functional map, adjusting the voxels in each lesioned brain region to the functional region with the highest correlation coefficient with the voxel, generating the brain functional map of the lesioned brain region, and combining it with the brain functional map of the non-lesioned brain region as a new whole-brain functional map, which is used as image signal of the whole brain functional map for the next recursive operation, and gradually adjusting the boundaries of these functional regions according to the subject's image signals of the lesioned brain regions (the recursive process will use the individual difference distribution of the patient's brain connectivity, as well as the subject's own signal-to-noise ratio of the brain images to determine the adjustment magnitude of the network boundary), until the results of the network profiling tend to be stabilized or the iteration termination conditions are reached, such as the number of iterations reaches the pre-set value, and the final brain functional map of the lesioned brain region of the subject is obtained.

Step 203, for each of the to-be-clinically-intervened voxels in the set of to-be-clinically-intervened voxels, brain functional region identifiers corresponding to the to-be-clinically-intervened voxels are determined based on the to-be-clinically-intervened voxels and the brain functional map.

Where the brain functional region representation includes brain functional region identifiers and invalid brain functional region identifiers in the brain functional map.

Clinical intervention includes influencing the development of a certain disease through various therapeutic means, such as surgical treatment, chemical drug treatment, radiotherapy, targeted therapy, immunotherapy, interventional therapy, and the like, which are commonly used in clinical practice.

Here, the set of to-be-clinically-intervened voxels is the set of voxels corresponding to the brain region of the subject to be clinically intervened. The set of to-be-clinically-intervened voxels corresponding to the brain region of the subject to be clinically intervened may be determined by projecting the brain region of the subject to be clinically intervened on the brain structural magnetic resonance imaging data and/or brain functional magnetic resonance imaging data of the subject. The subject's brain region to be clinically intervened may include a diseased brain structure region of the subject, e.g., a brain structure region of necrotic brain tissue resulting from a previous clinical intervention or from trauma, a tumor-occupied brain structure region, etc., which is only an example, and in practice, the subject's brain region to be clinically intervened may be determined based on a preoperative diagnosis of the subject.

By the above step 202, a brain functional map of the subject is obtained, and the brain functional map is capable of characterizing the division of brain functional regions of the subject, and by projecting the brain structural region corresponding to the brain region of the subject to be clinically intervened onto the brain functional map of the subject, the brain functional regions included in the brain structural region corresponding to the brain region of the subject to be clinically intervened can be determined, i.e., the brain functional regions of the brain region of the subject to be clinically intervened can be determined.

Step 204, the set of to-be-clinically-intervened voxels is divided according to the brain functional region identifiers corresponding to each to-be-clinically-intervened voxel, thereby obtaining at least one subset of to-be-clinically-intervened brain functional region voxels, with the to-be-clinically-intervened voxels in each subset of to-be-clinically-intervened brain functional region voxel corresponding to the same brain functional region identifier.

The to-be-clinical intervention voxels are voxels contained in the set of to-be-clinical intervention voxels.

Here, dividing the to-be-clinically-intervened voxels with the same brain functional region identifier into the same subset of to-be-clinically-intervened brain functional region voxels enables the division of the brain functional region of the to-be-clinically-intervened voxels within the target surgical region, wherein the to-be-clinically-intervened voxels in the subset of the to-be-clinically-intervened brain functional region voxels pertains to the same brain functional region, in order to facilitate the determination of the brain function lateralization of the subset of the to-be-clinically-intervened brain functional region voxels formed by the to-be-clinically-intervened voxels having the same brain functional region identifier on the basis of the same brain functional region.

Step 205, for each subset of to-be-clinically-intervened brain functional region voxels, a brain functional lateralization corresponding to the subset of to-be-clinically-intervened brain functional region voxels is determined based on the brain functional map.

In this application, the brain function lateralization of the brain functional region is expressed by using the Lateralization Index (LI).

In some optional embodiments, the above step 205 may specifically include:

determining the brain functional lateralization corresponding to the subset of to-be-clinically-intervened brain functional region voxels based on a hemispheric autonomy index (AI) of the brain functional region corresponding to the subset of to-be-clinically-intervened brain functional region voxels, specifically:

first, the LI of the brain functional region of the target surgical region is calculated by the following formula.

$$LI = \begin{cases} \dfrac{AI_L - AI_R}{AI_L + AI_R} & AI_L + AI_R > 0 \\ \dfrac{AI_R - AI_L}{AI_L + AI_R} & AI_L + AI_R < 0 \end{cases}$$

AIL: summing and/or averaging among the normalized AI or the AI of brain functional regions representing the left surgical region; AIR: summing and/or averaging among the normalized AI or the AI of brain functional regions representing the right surgical region.

The normalization is then performed for LI so that the range thereof falls between −1 and 1. In this application, a value of [−1,0) for the LI indicates that the brain function lateralization is skewed to the left, and a value of (0,1] for the LI indicates that the brain function lateralization is skewed to the right, and the size of the absolute value of the LI is positively correlated with the lateralization degree of brain function.

In the present application, the normalization of the LI may, for example, be performed using any of the following options 1 to 4:

Option 1, LI_norm = $(LI - LI(\min))/(LI(\max) - LI(\min))$;

LI_norm is the normalized lateralization index; LI(min) is the minimum value of the lateralization index; LI(max) is the maximum value of the lateralization index;

Option 2, LI_norm = $(LI - LI(\mathrm{mean}))/(LI(\max) - LI(\min))$;

LI(mean) is the mean value of the lateralization index;

Option 3, LI_norm = $lg(LI)$;

Option 4, LI_norm = $a\tan(LI)*2/\pi$.

For the calculation of AI, exemplarily, the calculation may be performed as follows:

Under the circumstance that each vertex/voxel in the brain functional magnetic resonance imaging data is considered as a region of interest (ROI), calculating, for each ROI, the strength of functional connectivity with the ipsilateral hemispheric ROI and the strength of functional connectivity with the contralateral hemispheric ROI.

A threshold (0.1-1) is set and the number of ipsilateral hemispheric connections Ni and the number of contralateral hemispheric connections Nc greater than the threshold were counted for each ROI.

The autonomy index AI is calculated by the following formula:

$$AI = N_i/H_i - N_c/H_c$$

wherein, $H_i$ is the total number of vertices/voxels of ipsilateral hemisphere, He is number of vertices/voxels of contralateral hemisphere.

In some optional embodiments, the above step 205 may also specifically include:

determining the brain functional lateralization corresponding to the subset of voxels of the brain functional region to be clinically intervened based on the areas of the functional region surface on the left and right sides of the brain functional region corresponding to the subset of to-be-clinically-intervened brain functional region voxels. The area of the functional region surface may be characterized as the area corresponding to the number of voxels of the brain functional region, calculated by the following formula.

$$LI = (L - R)/(L + R);$$

wherein L is the number of surface voxels in the left functional region and R is the number of surface voxels in the right functional region.

As shown in FIG. 2, in some optional embodiments, the above-described process 200 further comprises the following steps:

Step 206, for each subset of the to-be-clinically-intervened brain functional region voxels, a surgical risk value corresponding to the subset of the to-be-clinically-intervened brain functional region voxels is determined based on the brain functional lateralization corresponding to the subset of the to-be-clinically-intervened brain functional region voxels.

Step 207, for each subset of the to-be-clinically-intervened brain functional region voxels, determining a pixel value corresponding to the subset of the to-be-clinically-intervened brain functional region voxels based on the surgical risk value corresponding to the subset of the to-be-clinically-intervened brain functional region voxels, and presenting the subset of the to-be-clinically-intervened brain functional region voxels according to the determined pixel values.

In some optional implementations, the above step 207 may specifically include: presenting the pixel values in the brain function map corresponding to the subset of the to-be-clinically-intervened brain functional region voxels in accordance with the determined pixel values to obtain a risk map used to characterize the brain function region and brain function lateralization of the subset of the to-be-clinically-intervened brain functional region voxels in the target surgical region of the subject.

By determining the subset of the to-be-clinically-intervened brain functional region voxels in the target surgical region and determining the brain functional lateralization corresponding to the subsets of the to-be-clinically-intervened brain functional region voxels, an accurate localization of the brain functional region is realized in the target surgical region, and the risk map of the surgically relevant functional region is outlined. Risk map is able to present the importance of the function of the part to be resected in the target surgical region through the pixel values of the labeled voxels, and the risk of functional impairment of the patient after resection of the part, and the importance is positively correlated with the risk level, for example: red is important and high risk: yellow is average and medium risk; green is unimportant and low risk. The determination of risk map allows neurosurgeons to develop a personalized surgical plan suitable for the patient, shorten the operation time, improve the success rate of the operation, and reduce the risk of the patient experiencing functional impairment after the operation.

Figure 5A:
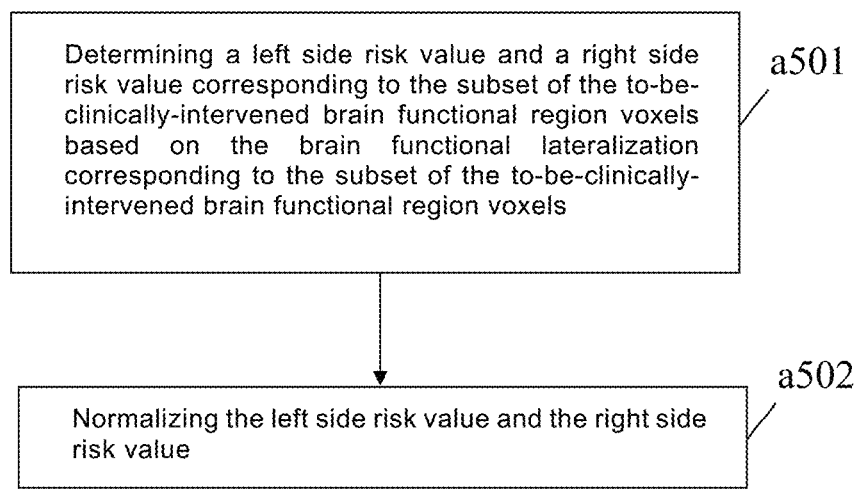
FIG. 5A is a schematic diagram of a disassembled flow of an embodiment of step 205 in the method for localizing and lateralizing brain functional regions shown in FIG. 2.

FIG. 5A is a schematic diagram of a disassembled flow of one embodiment of step 206 in the method for localizing and lateralizing brain functional regions shown in FIG. 2. The surgical risk values include a left side risk value and a right side risk value. In some optional embodiments, step 206 above may specifically include:

Step a501, determining a left-side risk value and a right-side risk value corresponding to the subset of the to-be-clinically-intervened brain functional region voxels based on the brain functional lateralization corresponding to the subset of the to-be-clinically-intervened brain functional region voxels.

Here, it can be assumed that the left-side risk value is A, the right-side risk value is B, and the lateralization index is C. The left-side risk value and the right-side risk value need to satisfy the following conditions at the same time:

$A+B=1$;                                    Condition 1:

$A-B=C$.                                    Condition 2:

Based on the above two conditions, the values of A and B can be obtained by substituting the values of C into the calculation.

Step a502, normalizing the left side risk value and the right side risk value.

Here, various implementations can be used to normalize A and B. For example, the quotient of A and B divided by the greater of A and B, respectively, can be determined as the values A_norm and B_norm normalized to A and B, i.e., A_norm=A/A=1 if A>B; B_norm=A/B; if A<B, then A_norm=A/B; and B_norm=B/B=1.

Correspondingly, the above step 206, may specifically comprise: visualizing the normalized left side risk value and the right side risk value.

Here, the visualization may be achieved, for example, by projecting the normalized left-side risk value and the right-side risk value on a brain functional map of the subject, for example, by corresponding the left-side risk value and the right-side risk value to two colors, and by setting pixel values corresponding to each voxel in the brain functional map according to the value size of the risk value, in order to achieve the visualization.

Figure 5B:
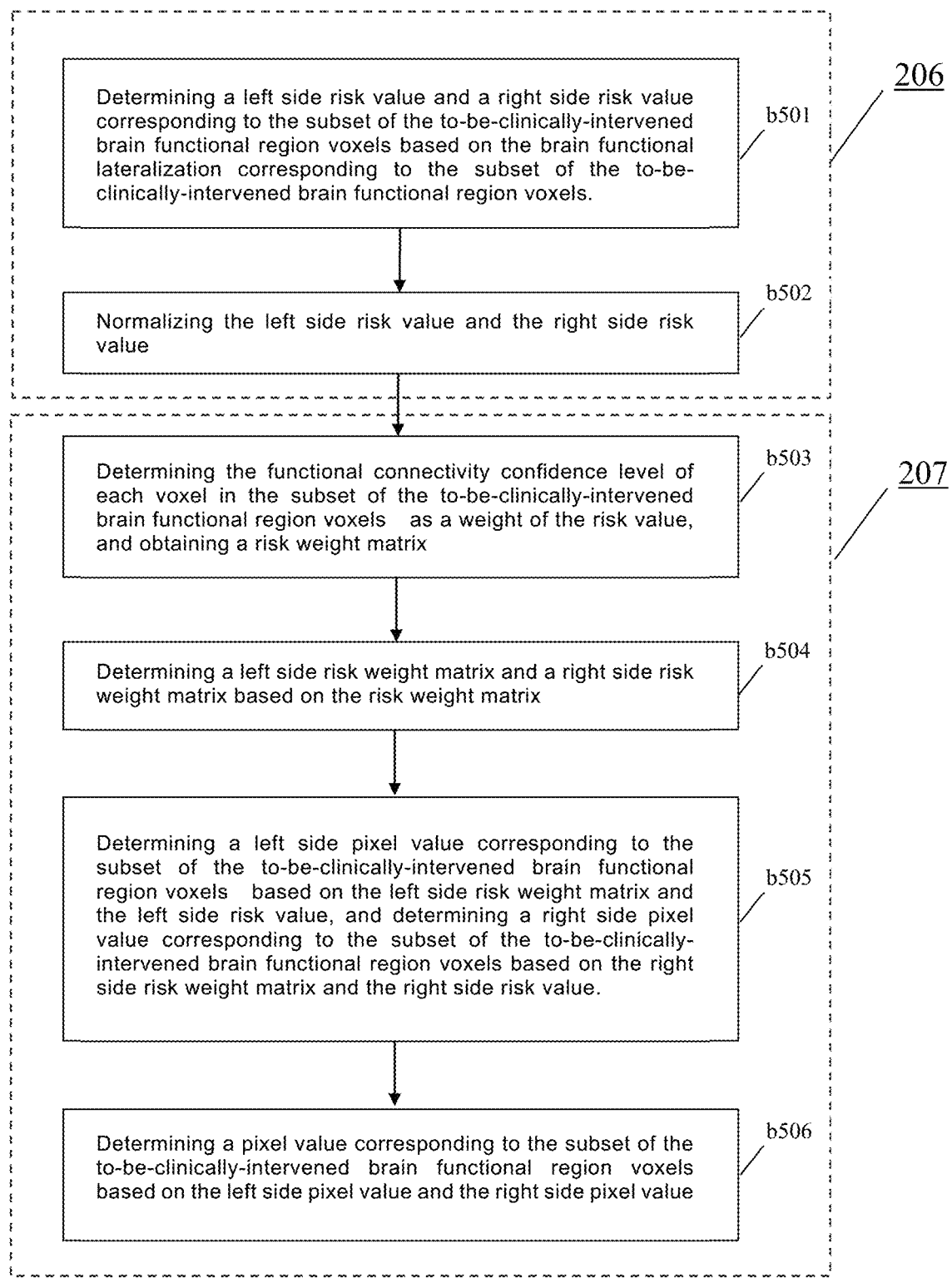
FIG. 5B is a schematic diagram of a disassembled flow of another embodiment of step 205 in the method for localizing and lateralizing brain functional regions shown in FIG. 2.

FIG. 5B is a schematic diagram of a disassembled flow of yet another embodiment of steps 206 and 207 of the method for localizing and lateralizing a brain functional region shown in FIG. 2. In some optional embodiments, the above step 206 may specifically include:

Step b501, determining a left-side risk value and a right-side risk value corresponding to the subset of the to-be-clinically-intervened brain functional region voxels based on the brain functional lateralization corresponding to the subset of the to-be-clinically-intervened brain functional region voxels.

Step b502, normalizing the left-side risk value and the right-side risk value.

Herein, the specific implementations and technical effects of steps b501 and b502 are substantially the same as those of a501 and a502 in the above embodiments, and will not be repeated herein.

Correspondingly, the above step 207 may specifically include:

Step b503, determining the functional connectivity confidence of each voxel in the subset of the to-be-clinically-intervened brain functional region voxels as a weight of the risk value, and obtaining a risk weight matrix.

During the process of determining the brain functional map of the subject, in addition to determining the brain functional regions of the subject, functional connectivity coefficients between each voxel in the brain functional magnetic resonance imaging data of the subject and each brain functional region are determined, where the functional connectivity coefficients are used to characterize the correlation between the voxels and the brain functional regions. The functional connectivity coefficients between any voxel and each brain functional region are ranked, and the ratio of the first-ranked functional connectivity coefficient to the second-ranked functional connectivity coefficient is used as the functional connectivity confidence value of the voxel. The functional connectivity confidence value of voxels reflects the confidence level of the brain functional area having the highest functional connectivity coefficient between the voxel and the brain functional area which the voxel pertains to. The higher the voxel's functional connectivity confidence value, the stronger the degree of confidence.

Step b504 determining a left side risk weight matrix and a right side risk weight matrix based on the risk weight matrix.

For example, it is assumed here that the risk weight matrix is W. Specifically, the above-described executive subject may set the value corresponding to vertices/voxels of the surgery-related right-side brain functional region in W to 0, i.e., obtaining the left-side brain risk weight matrix W(L), i.e., the left-side risk weight matrix, and set the value corresponding to vertices/voxels of the surgery-related left-side brain functional region in the risk weight matrix W to 0, i.e., obtaining the right-side brain risk weight matrix W(R), i.e., the right side risk weight matrix.

At step b505, determining a left side pixel value corresponding to the subset of the to-be-clinically-intervened brain functional region voxels based on the left side risk weight matrix and the left side risk value, and determining a right side pixel value corresponding to the subset of the to-be-clinically-intervened brain functional region voxels based on the right side risk weight matrix and the right side risk value.

Since the main structure of the human brain is divided as the left and right brains, and in practice, doing surgery requires a description that separates the left and right sides and the like, a left-side risk map and a right-side risk map can be determined. In this case, the left-side risk map is used to present the voxels of left-side risk in the target surgical region, and the right-side risk map is used to present the voxels of right-side risk in the target surgical region.

The left-side risk weight matrix W(L) is multiplied by the left-side normalized risk value A_norm to obtain the left-side risk map Riskmap(L), i.e., Riskmap(L)=W(L)*A_norm, and the right-side risk weight matrix W(R) is multiplied by the right-side normalized risk value B_norm to obtain the right-side risk map Riskmap(R), i.e., Riskmap(R)=W(R)*B_norm.

Step b506, determining the pixel values corresponding to the subset of the to-be-clinically-intervened brain functional region voxels based on the left side pixel values and the right side pixel values.

The pixel values corresponding to the subset of the to-be-clinically-intervened brain functional region voxels are obtained by combining the left-side pixel values and the right-side pixel values.

In some optional implementations, the above step b505 may specifically include: projecting the left-side pixel values correspondingly on the brain functional map to present a left-side risk map corresponding to the subset of the to-be-clinically-intervened brain functional region voxels of the subject; and projecting the right-side pixel values correspondingly on the brain functional map to present a right-side risk map corresponding to the subset of the to-be-clinically-intervened brain functional region voxels of the subject.

Correspondingly, the above step b506 may specifically comprise: combining the left-side risk map and the right-side risk map to obtain a risk map corresponding to the subset of the to-be-clinically-intervened brain functional region voxels.

The left and right side risk maps Riskmap(L) and Riskmap(R) of the target surgical region may also be combined together to obtain a risk map of the target surgical region.

The present application does not make specific limitations on the way of visualizing the risk map, and the above mentioned executing subject may select a combination of grayscale, color, and brightness for visualizing and displaying the risk map according to the actual surgical needs, and it is sufficient to be able to clearly display the risk of resecting the brain functional region of the target surgical region.

Embodiments of the present application provide a method for localizing and lateralizing a brain functional region which is used to locate the dominant side and functional region of the brain function based on the brain functional region of an individual subject and by using brain functional magnetic resonance data. Conventional preoperative lateralizing and localizing methods are unable to safely and efficiently determine the brain functional dominant side and functional regions. The use of magnetic resonance as well as functional magnetic resonance imaging allows non-invasive detection of human brain function. The present application utilizes brain functional magnetic resonance imaging to accurately localize and lateralize the brain function based on personalized brain functional region dissection technology, which provides strong theoretical support and technical support for the surgeon's brain surgery planning. It can effectively solve the problems of inaccurate localizing and lateralization of functional regions and postoperative complications caused by the traditional methods that do not take into account individual structural or functional differences. The precise preoperative localizing and lateralization technology is developed, and precise localizing and lateralization are performed through personalized brain functional region segmentation technology.

Figure 6:
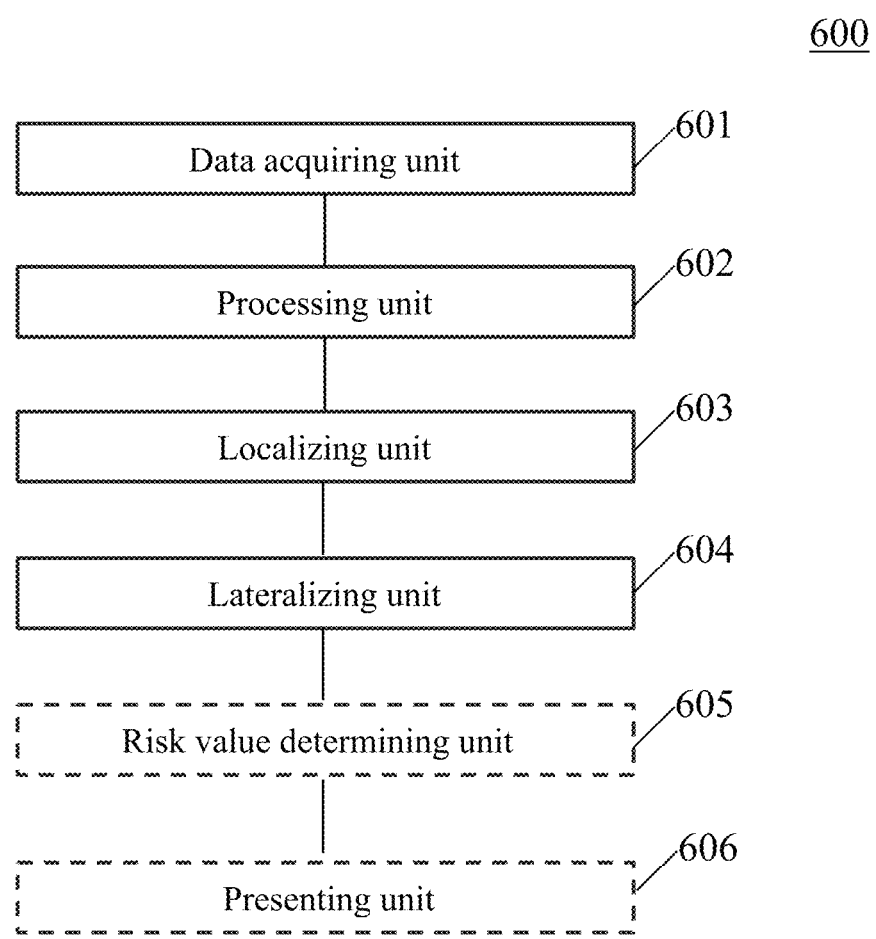
FIG. 6 is a schematic structural diagram of an embodiment of a localizing and lateralizing device for brain functional region according to the present application.

Referring further to FIG. 6, as an implementation of the method shown in each of the above figures, the present application provides an embodiment of a device for localizing and lateralizing a brain functional region, which embodiment corresponds to the embodiment of the method shown in FIG. 2, and which can be specifically applied in various electronic devices.

As shown in FIG. 6, the device for localizing and lateralizing a brain functional region 600 of this embodiment includes: a data acquiring unit 601, a processing unit 602, a localizing unit 603, and a lateralizing unit 604.

The data acquiring unit 601 is configured to acquire brain structural magnetic resonance imaging data and brain functional magnetic resonance imaging data of the subject.

The processing unit 602 is configured to determine a brain functional map of the subject based on the brain structural magnetic resonance imaging data and the brain functional magnetic resonance imaging data, wherein the brain functional map comprises brain functional region identifiers of at least two brain functional regions and corresponding sets of voxels.

The localizing unit 603 is configured to determine, for each of the to-be-clinically-intervened voxels in the set of to-be-clinically-intervened voxels, the brain functional region identifiers corresponding to the to-be-clinically-intervened voxel based on the to-be-clinically-intervened voxel and the brain functional map, wherein the brain functional region identifiers comprises the brain functional region identifiers in the brain functional map.

The lateralizing unit 604 is configured to divide the set of to-be-clinically-intervened voxels in accordance with the brain functional region identifier corresponding to each to-be-clinically-intervened voxel, thereby obtaining at least one subset of voxels to-be-clinically-intervened brain functional region, with the to-be-clinically-intervened voxels in each of the subsets of the to-be-clinically-intervened brain functional region voxels corresponding to the same brain functional region identifiers, and for each subset of the to-be-clinically-intervened brain functional region voxels, based on the brain functional map to determine the brain functional lateralization corresponding to that subset of to-be-clinically-intervened brain functional region voxels.

In some optional embodiments, the above-described device for localizing and lateralizing the brain functional region 600 may further comprise:

a risk value determining unit 605 configured to determine, for each subset of the to-be-clinically-intervened brain functional region voxels, a surgical risk value corresponding to the subset of the to-be-clinically-intervened brain functional region voxels based on the functional lateralization corresponding to the subset of the to-be-clinically-intervened brain functional region voxels.

In some optional embodiments, the above-described device for localizing and lateralizing the brain functional region 600 may further comprise:

a presenting unit 606 configured to determine, for each subset of the to-be-clinically-intervened brain functional region voxels, the pixel values corresponding to the subset of the to-be-clinically-intervened brain functional region voxels based on the surgical risk value corresponding to the subset of the to-be-clinically-intervened brain functional region voxels, and to present the subset of the to-be-clinically-intervened brain functional region voxels in accordance with the determined pixel values.

In some optional embodiments, the processing unit 602, is further configured to:

determine, based on the brain structure magnetic resonance imaging data, whether the brain structure of the subject has lesion;

determine a brain functional map of the subject based on the brain functional magnetic resonance imaging data if the brain structure of the subject does not have any lesion.

In some optional embodiments, the processing unit 602, is further configured to:

determine regions of the lesioned brain structure of the subject if the brain structure of the subject has lesion;

determine a lesioned brain region and a non-lesioned brain region of the subject based on the lesioned brain structure region, wherein the lesioned brain region comprises M voxels, M being a positive integer greater than or equal to 2;

determine a brain functional map of the non-lesioned brain region based on functional magnetic resonance imaging data of the brain, wherein the brain functional map of the non-lesioned brain region comprises N brain functional regions, N being a positive integer greater than or equal to 2;

determine a correlation between each voxel in the M voxels corresponding to the lesioned brain region and each brain functional region in the N brain functional regions;

determine, for each voxel in the M voxels, the brain functional region corresponding to the voxel, according to the correlation between the voxel and each brain functional region in the N brain functional regions according to a predetermined functional region classification rule, to obtain a brain functional map of the subject.

In some optional embodiments, the processing unit 602, is further configured to:

identify the brain functional region among the N brain functional regions having the highest correlation with the voxel as the brain functional region corresponding to the voxel.

In some optional embodiments, the processing unit 602, is further configured to:

in response to determining that each of the N brain functional regions has a correlation with the voxels that is less than a predetermined correlation threshold, the brain functional region corresponding to the voxels is determined to be an invalid brain functional region.

In some optional implementations, the processing unit 602, is further configured to:

determine the brain functional regions with the highest correlation with the voxels among the N brain functional regions as the brain functional regions corresponding to the voxels, obtaining the first iterative brain functional map of the lesioned brain regions;

perform the following iterative operation: combining the first iterative brain functional map of the lesioned brain regions with the brain functional map of the non-lesioned brain regions to obtain the iterative brain functional map, the iterative brain functional map comprising N iterative brain functional regions; determining correlation between the voxels and each of the N iterative brain functional regions; and determining the brain functional regions with the highest correlations with the voxel among the N brain functional regions as a brain functional region corresponding to the voxel, then obtaining the second iterative brain functional map of the lesioned brain regions; determining whether the match between the second iterative brain functional map of the lesioned brain region and the first iterative brain functional map of the lesioned brain region is greater than a predetermined match threshold value; If yes, the second iterative brain functional map of the lesioned brain region is identified as the brain functional map of the lesioned brain region, ending the iterative operation, and the brain functional map of the lesioned brain region is used to characterize the brain functional region corresponding to the voxel, if not, continuing the iterative operation after updating the first iterative brain functional map of the lesioned brain region to be the second iterative brain functional map of the lesioned brain region.

In some optional embodiments, the lateralizing unit 604, is further configured to:

determine a brain functional lateralization corresponding to the subset of the to-be-clinically-intervened brain functional region voxels based on a hemispheric autonomy index of the brain functional region corresponding to the subset of the to-be-clinically-intervened brain functional region voxels;

or, determine the brain functional lateralization corresponding to the subset of the to-be-clinically-intervened brain functional region voxels based on the areas of the left and right lateral functional region surfaces of the brain functional regions corresponding to the subset of the to-be-clinically-intervened brain functional region voxels.

In some optional implementations, the risk value determining unit 605, is further configured to:

determine, based on the functional lateralization corresponding to the subset of the to-be-clinically-intervened brain functional region voxels, a left side risk value and a right side risk value corresponding to the subset of the to-be-clinically-intervened brain functional region voxels.

In some optional embodiments, the brain functional map further comprises each of functional connectivity confidence levels between voxels; and, the presenting unit 606, is further configured to:

determine the functional connectivity confidence level for each voxel in the subset of the to-be-clinically-intervened brain functional region voxels as a weight of a risk value to obtain a risk weight matrix;

determine a left-side risk weight matrix and a right-side risk weight matrix based on the risk weight matrix;

determine a left side pixel value corresponding to the subset of the to-be-clinically-intervened brain functional region voxels based on the left side risk weight matrix and the left side risk value;

determine a right side pixel value corresponding to the subset of the to-be-clinically-intervened brain functional region based on the right side risk weight matrix and the right side risk value;

determine a pixel value corresponding to the subset of the to-be-clinically-intervened brain functional region voxels based on the left side pixel value and the right side pixel value.

It should be noted that, for implementation details and technical effects of each unit in the device for localizing and lateralizing the brain functional region provided in the present disclosure, reference may be made to other embodiments in the present disclosure, and the details will be omitted herein.

Figure 7:
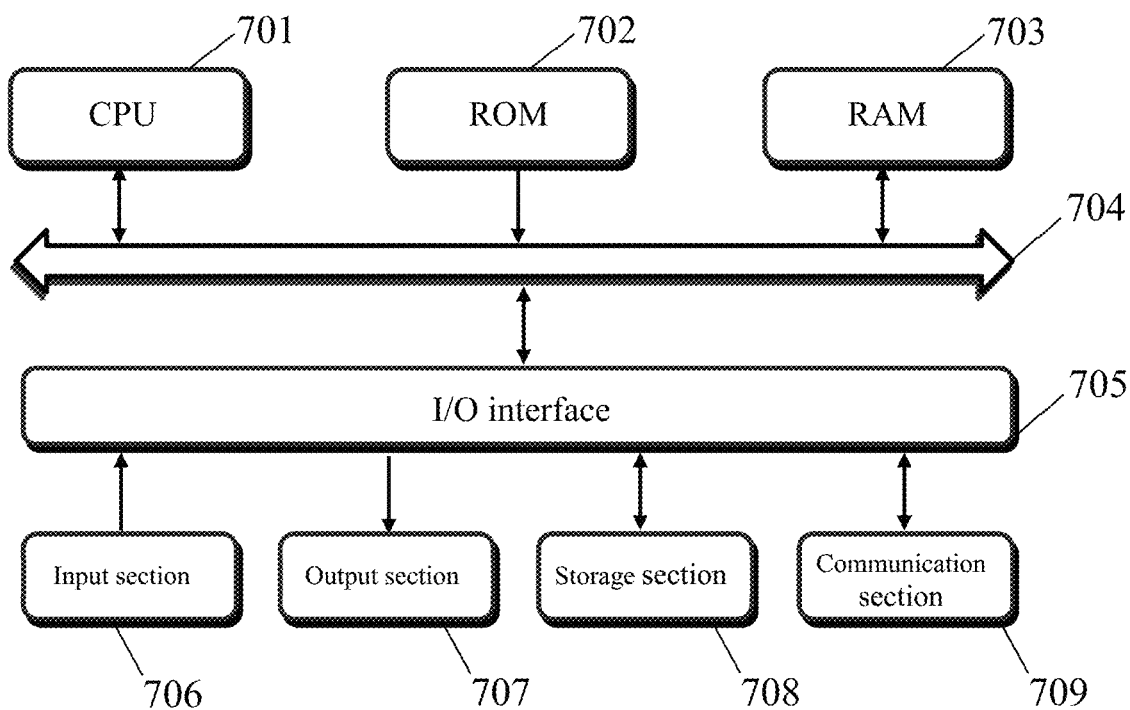
FIG. 7 is a schematic diagram of a structure of a computer system suitable for use in implementing a terminal equipment or server of the present application.

Referring now to FIG. 7, it shows a schematic block diagram of a computer system 700 suitable for use in implementing a terminal device or server of the present disclosure. The terminal device or server shown in FIG. 7 is only an example, and should not bring any limitation to the function and the use range of the present disclosure.

As shown in FIG. 7, the computer system 700 includes a Central Processing Unit (CPU) 701 which can perform various appropriate actions and processes according to a program stored in a Read Only Memory (ROM) 702 or a program loaded from a storage section 708 into a Random Access Memory (RAM) 703. In the RAM 703, various programs and data necessary for the operation of the computer system 700 are also stored. The CPU 701, ROM 702, and RAM 703 are connected to each other via a bus 704. An Input/Output (I/O) interface 705 is also connected to the bus 704.

The following components are connected to the I/O interface 705: an input section 706 including a keyboard, a mouse, and the like; an output section 707 including such as a Cathode Ray Tube (CRT), a Liquid Crystal Display (LCD), and a speaker; a storage section 708 including a hard disk and the like; and a communication section 709 including a network interface card such as a LAN (Local Area Network) card, a modem. The communication section 709 performs communication processing via a network such as the Internet.

In particular, the processes described above with reference to the flow charts may be implemented as computer software programs, according to embodiments of the present disclosure. For example, embodiments of the present disclosure include a computer program product including a computer program carried on a computer-readable medium, the computer program including program code for performing the method illustrated by the flow chart. In such an embodiment, the computer program can be downloaded and installed from the network via communication section 709. The computer program performs the above-described functions defined in the method of the present disclosure when executed by the Central Processing Unit (CPU) 701. It should be noted that the computer readable medium of the present disclosure can be a computer readable signal medium or a computer readable storage medium or any combination of both. A computer readable storage medium may be, for example, but not limited to, an electronic, magnetic, optical, electromagnetic, infrared, or semiconductor system, apparatus, or device, or any combination thereof. More specific examples of the computer readable storage medium may include, but are not limited to: an electrical connection having one or more wires, a portable computer disk, a hard disk, a Random Access Memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination thereof. In the present disclosure, the computer readable storage medium may be any tangible medium that can contain, or store a program for use by or in connection with an instruction execution system, apparatus, or device. In contrast, in the present disclosure, a computer-readable signal medium may include a propagated data signal carried with computer-readable program code therein in baseband or as part of a carrier wave Such a propagated data signal may take any of a variety of forms, including, but not limited to, electro-magnetic signals, optical signals, or any suitable combination thereof. The computer-readable signal medium may be any computer readable medium that is not a computer readable storage medium and that can communicate, propagate, or transmit a program for use by or in connection with an instruction execution system, apparatus, or device. Program code embodied on a computer readable medium may be transmitted using any appropriate medium, including but not limited to: wireless, wire, fiber optic cable, RF, etc., or any suitable combination of thereof.

Computer program code for carrying out operations for the present disclosure may be written in one or more programming language(2) or any combination thereof, including object oriented programming languages such as Java, Smalltalk, C++, Python, and conventional procedural programming languages, such as "C" programming language or similar programming languages. The program code may execute entirely on the user's computer, partly on the user's computer, as a stand-alone software package, partly on the user's computer and partly on a remote computer or entirely on the remote computer or server. In the scenario associated with the remote computer, the remote computer may be connected to the user's computer through any type of networks, including a Local Area Network (LAN) or a Wide Area Network (WAN), or the connection may be made to an external computer (for example, through the Internet using an Internet service provider).

The flowchart and block diagrams in the figures illustrate the architecture, functionality, and operation of possible implementations of systems, methods and computer program products according to various embodiments of the present disclosure. In this regard, each block in the flowchart or block diagrams may represent a module, program segment, or portion of code, which includes one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The units described in this disclosure may be implemented by software or hardware. The described units may also be provided in a processor, which may be described as: a processor includes a scan data acquiring unit, a processing unit, a localizing unit, and a lateralizing unit. The names of the units do not constitute a limitation on the units themselves in some way.

As another aspect, the present disclosure also provides a computer-readable medium, which may be contained in the device described in the above embodiments; or may be separate and not assembled into the device. The computer readable medium carries one or more programs which, when executed by the device, causes the device to: obtaining brain structural magnetic resonance imaging data and brain functional magnetic resonance imaging data of the subject; based on the brain structural magnetic resonance imaging data and the brain functional magnetic resonance imaging data, determining a brain functional map of the subject, wherein the brain functional map comprises brain functional area identifiers of at least two brain functional regions and a corresponding set of voxels; for each of the to-be-clinically-intervened voxels in the set of to-be-clinically-intervened voxels, determining a corresponding brain functional region identifier of the to-be-clinically-intervened voxel according to the to-be-clinically-intervened voxel and the brain functional map, wherein the brain functional region identifier includes the brain functional region identifier in the brain functional map; dividing the set of to-be-clinically-intervened voxels according to the brain functional region identifier corresponding to each to-be-clinically-intervened voxel to obtain at least one subset of the to-be-clinically-intervened brain functional region voxels, and to-be-clinically-intervened voxels in each subset of to-be-clinically-intervened brain functional region voxels correspond to the same brain functional region identifier; for each subset of to-be-clinically-intervened brain functional region voxels, determining the brain functional lateralization corresponding to the subset of the to-be-clinically-intervened brain functional region voxels based on brain functional map.

The foregoing description is only exemplary of the preferred embodiments of the disclosure and is illustrative of the principles of the technology employed. It will be appreciated by those skilled in the art that the scope of the invention in the present disclosure is not limited to the technical solutions defined by the specific combination of the above-mentioned technical features, but also encompasses other technical solutions in which any combination of the above-mentioned features or their equivalents is made without departing from the inventive concept of the disclosure. For example, such other technical solutions may be defined by replacing the above features and the technical features disclosed in the present disclosure (but not limited to) having similar functions with each other.

The technical solutions described in the embodiments of the present disclosure can be arbitrarily combined without conflict.

The above description is only for the specific embodiments of the present disclosure, but the protection scope of the present disclosure is not limited thereto, and any person skilled in the art can easily think of the changes or substitutions within the technical scope of the present disclosure, and shall cover the scope of the present disclosure. Therefore, the protection scope of the present disclosure shall be subject to the protection scope of the appended claims.

What is claimed is:

1. A method of localizing and lateralizing brain functional regions, comprising:
    acquiring brain structural magnetic resonance imaging data and brain functional magnetic resonance imaging data of a subject;
    determining a brain functional map of the subject based on the brain structural magnetic resonance imaging data and the brain functional magnetic resonance imaging data, wherein the brain functional map comprises brain functional region identifiers of at least two brain functional regions and a corresponding set of voxels;
    for each to-be-clinically-intervened voxel in a set of to-be-clinically-intervened voxels, determining the corresponding brain functional region identifiers for the to-be-clinically-intervened voxel based on the to-be-clinically-intervened voxel and the brain functional map, wherein the brain functional region identifiers comprises the brain functional region identifier in the brain functional map;

dividing the set of to-be-clinically-intervened voxels in accordance with the brain functional region identifier corresponding to each to-be-clinically-intervened voxel to obtain at least one subset of to-be-clinically-intervened brain functional region voxels, with to-be-clinically-intervened voxels in each subset of the to-be-clinically-intervened brain functional region voxels corresponding to a same brain functional region identifier;

for each subset of to-be-clinically-intervened brain functional region voxels, determining, based on the brain functional map, a brain functional lateralization corresponding to the subset of to-be-clinically-intervened brain functional region voxels.

2. The method according to claim 1, wherein the method further comprises:

for each subset of to-be-clinically-intervened brain functional region voxels, determining a surgical risk value corresponding to the subset of to-be-clinically-intervened brain functional region voxels, based on the brain functional lateralization corresponding to the subset of to-be-clinically-intervened brain functional region voxels.

3. The method according to claim 2, wherein the method further comprises:

for each subset of to-be-clinically-intervened brain functional region voxels, determining a pixel value corresponding to the subset of to-be-clinically-intervened brain functional region voxels, based on the surgical risk value corresponding to the subset of to-be-clinically-intervened brain functional region voxels, and presenting the subset of voxels of to-be-clinically-intervened brain functional regions in accordance with the determined pixel value.

4. The method according to claim 3, wherein the surgical risk value comprises a left side risk value and a right side risk value; and determining a surgical risk value corresponding to the subset of the to-be-clinically-intervened brain functional region voxels based on the brain function lateralization corresponding to the subset of the to-be-clinically-intervened brain functional region voxels, comprising:

determining the left side risk value and the right side risk value corresponding to the subset of the to-be-clinically-intervened brain functional region voxels based on the brain function lateralization corresponding to the subset of the to-be-clinically-intervened brain functional region voxels.

5. The method according to claim 4, wherein the brain functional map further comprises a functional connectivity confidence level between two different voxels; and the step of determining the pixel value corresponding to the subset of the to-be-clinically-intervened brain functional region voxels based on the surgical risk value corresponding to the subset of the to-be-clinically-intervened brain functional region voxels, further comprising:

determining the functional connectivity confidence level of each voxel of the subset of the to-be-clinically-intervened brain functional region voxels as a weight of the risk value to obtain a risk weight matrix;

determining a left side risk weight matrix and a right side risk weight matrix based on the risk weight matrix;

determining a left side pixel value corresponding to the subset of the to-be-clinically-intervened brain functional region voxels based on the left side risk weight matrix and the left side risk value;

determining a right side pixel value corresponding to the subset of the to-be-clinically-intervened brain functional region voxels based on the right side risk weight matrix and the right side risk value;

determining a pixel value corresponding to the subset of the to-be-clinically-intervened brain functional region voxels based on the left side pixel value and the right side pixel value.

6. The method according to claim 3, wherein determining a brain functional map of the subject based on the brain structural magnetic resonance imaging data and said brain functional magnetic resonance imaging data, comprising:

determining, based on the brain structural magnetic resonance imaging data, whether the brain structure of the subject has lesion or not;

if the brain structure of the subject has no lesion, determining a brain functional map of the subject based on the brain functional magnetic resonance imaging data.

7. The method according to claim 3, wherein, determining, for each subset of the to-be-clinically-intervened brain functional region voxels, a brain functional lateralization corresponding to the subset of the to-be-clinically-intervened brain functional region voxels based on the brain functional map, comprising:

determining, based on a hemispheric autonomy index of the brain functional region corresponding to the subset of the to-be-clinically-intervened brain functional region voxels, the brain functional lateralization corresponding to the subset of the to-be-clinically-intervened brain functional region voxels;

or, determining the brain functional lateralization corresponding to the subset of the to-be-clinically-intervened brain functional region voxels based on areas of left and right lateral functional region surfaces of the brain functional region corresponding to the subset of the to-be-clinically-intervened brain functional region voxels.

8. The method according to claim 2, wherein determining a brain functional map of the subject based on the brain structural magnetic resonance imaging data and said brain functional magnetic resonance imaging data, comprising:

determining, based on the brain structural magnetic resonance imaging data, whether the brain structure of the subject has lesion or not;

if the brain structure of the subject has no lesion, determining a brain functional map of the subject based on the brain functional magnetic resonance imaging data.

9. The method according to claim 2, wherein, determining, for each subset of the to-be-clinically-intervened brain functional region voxels, a brain functional lateralization corresponding to the subset of the to-be-clinically-intervened brain functional region voxels based on the brain functional map, comprising:

determining, based on a hemispheric autonomy index of the brain functional region corresponding to the subset of the to-be-clinically-intervened brain functional region voxels, the brain functional lateralization corresponding to the subset of the to-be-clinically-intervened brain functional region voxels;

or, determining the brain functional lateralization corresponding to the subset of the to-be-clinically-intervened brain functional region voxels based on areas of left and right lateral functional region surfaces of the brain functional region corresponding to the subset of the to-be-clinically-intervened brain functional region voxels.

10. The method according to claim 1, wherein determining a brain functional map of the subject based on the brain structural magnetic resonance imaging data and said brain functional magnetic resonance imaging data, comprising:

determining, based on the brain structural magnetic resonance imaging data, whether the brain structure of the subject has lesion or not;

if the brain structure of the subject has no lesion, determining a brain functional map of the subject based on the brain functional magnetic resonance imaging data.

11. The method according to claim 10, wherein determining the brain functional map of the subject based on the brain structure magnetic resonance imaging data and the brain function magnetic resonance imaging data, further comprising:

determining a lesioned brain region and a non-lesioned brain region of the subject if the subject has a lesioned brain structure, wherein the lesioned brain region comprises M voxels, M being a positive integer greater than or equal to 2;

determining a brain functional map of the non-lesioned brain region based on the brain functional magnetic resonance imaging data, the brain functional map of the non-lesioned brain region comprising N brain functional regions, N being a positive integer greater than or equal to 2;

determining a correlation between each voxel in M voxels corresponding to the lesioned brain region and each brain functional region in the N brain functional regions;

for each voxel in the M voxel, determining, based on the correlation between the voxel and each of the N brain functional regions, the brain functional region corresponding to the voxel in accordance with a predetermined functional region classification rule, in order to obtain the brain functional map of the subject.

12. The method according to claim 11, wherein determining, based on the correlation between the voxel and each of the N brain functional regions, the brain functional region corresponding to the voxel in accordance with a predetermined functional region classification rule comprises:

determining the brain functional region among the N brain functional regions having the highest correlation with the voxel as a brain functional region corresponding to the voxel.

13. The method according to claim 11, wherein determining, based on the correlation between the voxel and each of the N brain functional regions, the brain functional region corresponding to the voxel in accordance with a predetermined functional region classification rule comprises:

in response to determining that the correlation between the voxel and each brain functional region of the N brain functional regions is less than a preset correlation threshold, determining the brain functional region corresponding to the voxel as an invalid brain functional region.

14. The method according to claim 11, wherein determining, based on the correlation between the voxel and each of the N brain functional regions, the brain functional region corresponding to the voxel in accordance with a predetermined functional region classification rule comprises:

determining the brain functional region with the highest correlation with the voxel among the N brain functional regions as the brain functional region corresponding to the voxel, and obtaining a first iterative brain functional map of a lesioned brain region;

performing the following iterative operation:

combining the first iterative brain functional map of the lesioned brain region with the brain functional map of the non-lesioned brain region to obtain an iterative brain functional map, the iterative brain functional map comprising N iterative brain functional regions;

determining a correlation between the voxel and each iterative brain functional region among the N iterative brain functional regions;

among the N brain functional regions, identifying the brain functional region with the highest correlation to the voxel as the brain functional region corresponding to the voxel, and obtaining a second iterative brain functional map of the lesioned brain region;

determining whether the degree of match between the second iterative brain functional map of the lesioned brain region and the first iterative brain functional map of the lesioned brain region is greater than a preset threshold value of the degree of match;

if yes, determining the second iterative brain functional map of the lesioned brain region as the brain functional map of the lesioned brain region, terminating the iterative operation, the brain functional map of the lesioned brain region is used to characterize the brain functional region corresponding to the voxel;

if not, updating the first iterative brain functional map of the lesioned brain region to be the second iterative brain functional map of the lesioned brain region and then continuing the iterative operation.

15. The method according to claim 1, wherein, determining, for each subset of the to-be-clinically-intervened brain functional region voxels, a brain functional lateralization corresponding to the subset of the to-be-clinically-intervened brain functional region voxels based on the brain functional map, comprising:

determining, based on a hemispheric autonomy index of the brain functional region corresponding to the subset of the to-be-clinically-intervened brain functional region voxels, the brain functional lateralization corresponding to the subset of the to-be-clinically-intervened brain functional region voxels;

or, determining the brain functional lateralization corresponding to the subset of the to-be-clinically-intervened brain functional region voxels based on areas of left and right lateral functional region surfaces of the brain functional region corresponding to the subset of the to-be-clinically-intervened brain functional region voxels.

16. An electronic apparatus, comprising:

one or more processors; and a storage device, having one or more programs stored thereon, wherein the one or more programs, when executed by the one or more processors, causes the one or more processors to execute the method according to claim 1.

17. A non-transitory computer readable storage medium, having a computer program stored thereon, wherein the computer program, when executed by one or more processors, executes the method according to claim 1.

18. A device for localizing and lateralizing a brain functional region, comprising:

a data acquiring circuit, configured to acquire brain structural magnetic resonance imaging data and brain functional magnetic resonance imaging data of a subject;

a processing circuit, configured to determine a brain functional map of the subject based on the brain structural magnetic resonance imaging data and the brain functional magnetic resonance imaging data, wherein the brain functional map comprises brain functional region identifiers of at least two brain functional regions and a corresponding set of voxels;

a localizing circuit, configured to determine, for each to-be-clinically-intervened voxel in a set of to-be-clinically-intervened voxels, a brain functional region identifier corresponding to the to-be-clinically-intervened voxel based on the to-be-clinically-intervened voxel and the brain functional map, wherein the brain functional region identifier comprises the brain functional region identifier in the brain functional map;

a lateralizing circuit, configured to divide the set of to-be-clinically-intervened voxels in accordance with the brain functional region identifier corresponding to the respective to-be-clinically-intervened voxel, obtain at least one subset of the to-be-clinically-intervened brain functional region voxels, to-be-clinically-intervened voxels in each subset of the to-be-clinically-intervened brain functional region voxels correspond to the same brain functional region identifier, and for each subset of the to-be-clinically-intervened brain functional region voxels, based on the brain functional map, determine brain functional lateralization corresponding to the subset of the to-be-clinically-intervened brain functional region voxels.

19. The device according to claim 18, wherein the device further comprises:

a risk value determining circuit, configured to determine, for each subset of to-be-clinically-intervened brain functional region voxels, a surgical risk value corresponding to the subset of to-be-clinically-intervened brain functional region voxels based on the brain function lateralization corresponding to the subset of the to-be-clinically-intervened brain functional region voxels.

20. The device according to claim 19, wherein the device further comprises:

a presenting circuit, configured to determine, for each subset of the to-be-clinically-intervened brain functional region voxels, a pixel value corresponding to the subset of the to-be-clinically-intervened brain functional region voxels, based on the surgical risk value corresponding to the subset of the to-be-clinically-intervened brain functional region voxels, and to present the subset of the to-be-clinically-intervened brain functional region voxels accordance with the determined pixel value.

* * * * *